United States Patent
Stafford

(10) Patent No.: US 10,641,758 B2
(45) Date of Patent: May 5, 2020

(54) APPARATUS, SYSTEMS, AND METHODS FOR ENHANCING HYDROCARBON EXTRACTION AND TECHNIQUES RELATED THERETO

(71) Applicant: Sherry L Stafford, The Woodlands, TX (US)

(72) Inventor: Sherry L Stafford, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 204 days.

(21) Appl. No.: 15/229,260

(22) Filed: Aug. 5, 2016

(65) Prior Publication Data

US 2017/0059544 A1  Mar. 2, 2017

Related U.S. Application Data

(60) Provisional application No. 62/212,761, filed on Sep. 1, 2015.

(51) Int. Cl.

| | |
|---|---|
| *C10G 1/04* | (2006.01) |
| *G01N 33/24* | (2006.01) |
| *G01N 21/33* | (2006.01) |
| *G01N 21/359* | (2014.01) |

(52) U.S. Cl.
CPC ........... *G01N 33/241* (2013.01); *C10G 1/045* (2013.01); *G01N 21/33* (2013.01); *G01N 21/359* (2013.01); *C10G 2300/10* (2013.01)

(58) Field of Classification Search
CPC ........ G01N 11/00; G01N 21/00; G01N 21/33; G01N 21/35; G01N 21/3563; G01N 33/24; G01N 33/241; G01N 33/222; G01N 33/26; G01N 33/28; C10G 1/00; C10G 1/008;
(Continued)

(56) References Cited

U.S. PATENT DOCUMENTS

| | | |
|---|---|---|
| 4,433,239 A | 2/1984 | Thompson |
| 5,781,336 A | 7/1998 | Coon et al. |
| 6,208,459 B1 | 3/2001 | Coon et al. |

(Continued)

FOREIGN PATENT DOCUMENTS

| | | |
|---|---|---|
| CA | 2235073 A1 | 10/1996 |
| CA | 2526854 A1 | 9/2001 |

(Continued)

OTHER PUBLICATIONS

Kansas Geologicla Survey, Open-file Report 2004-38, Chapter 1 Introduction and Chapter 5 Sequence Stratigraphy (Year: 2004).*

(Continued)

*Primary Examiner* — Prem C Singh
*Assistant Examiner* — Brandi M Doyle
(74) *Attorney, Agent, or Firm* — ExxonMobil Upstream Research Company—Law Department

(57) ABSTRACT

Provided are apparatus and systems using mine spectroscopic data at various stages of the hydrocarbon extraction process. The spectrometers may be mounted on various equipment components at the various stages of the hydrocarbon extraction process to passively collect energy reflected from objects. The obtained data may be used to determine mineralogy, bitumen saturation, bitumen viscosity, and grain size distribution in the mining operations.

18 Claims, 11 Drawing Sheets

(58) Field of Classification Search
CPC .......... C10G 1/04; C10G 1/042; C10G 1/045;
C10G 1/047
See application file for complete search history.

(56) References Cited

U.S. PATENT DOCUMENTS

| | | | |
|---|---|---|---|
| 6,554,368 | B2 | 4/2003 | Drake et al. |
| 6,768,115 | B2 | 7/2004 | Mikula et al. |
| 6,869,147 | B2 | 3/2005 | Drake et al. |
| 6,929,330 | B2 | 8/2005 | Drake et al. |
| 7,067,811 | B2 | 6/2006 | Long et al. |
| 7,369,229 | B2 | 5/2008 | Bissett, III et al. |
| 7,399,406 | B2 | 7/2008 | Mikula et al. |
| 7,718,956 | B2 | 5/2010 | Ferguson |
| 7,728,286 | B2 | 6/2010 | Ferguson |
| 8,117,891 | B2 | 2/2012 | Graeffe et al. |
| 8,315,838 | B2 | 10/2012 | Durrant-Whyte et al. |
| 8,336,370 | B2 | 12/2012 | Larter et al. |
| 8,547,096 | B2 | 10/2013 | Kamar et al. |
| 8,857,915 | B2 | 10/2014 | Nieto et al. |
| 9,016,399 | B2 | 4/2015 | Pelletier et al. |
| 9,087,338 | B2 | 7/2015 | Levine et al. |
| 2009/0071239 | A1 | 3/2009 | Rojas et al. |
| 2010/0132450 | A1 | 6/2010 | Pomerantz et al. |
| 2010/0207018 | A1 | 8/2010 | Djordjevic et al. |
| 2011/0042143 | A1 | 2/2011 | Auranen et al. |
| 2012/0306257 | A1 | 12/2012 | Silversides et al. |
| 2013/0169961 | A1 | 7/2013 | Kraft |
| 2013/0327683 | A1 | 12/2013 | Rivard et al. |
| 2014/0197316 | A1* | 7/2014 | Kadali ................ G01N 21/274 250/339.11 |
| 2014/0208826 | A1 | 7/2014 | Larter et al. |
| 2014/0326885 | A1 | 11/2014 | Davis et al. |
| 2014/0347472 | A1 | 11/2014 | Davis et al. |
| 2015/0068806 | A1 | 3/2015 | Duran Toro et al. |
| 2015/0323516 | A1 | 11/2015 | Washburn |
| 2015/0337208 | A1 | 11/2015 | Litz et al. |
| 2015/0337220 | A1 | 11/2015 | Litz et al. |
| 2016/0033676 | A1 | 2/2016 | Robinson et al. |

FOREIGN PATENT DOCUMENTS

| | | |
|---|---|---|
| CA | 2583508 A1 | 9/2001 |
| CA | 2583513 A1 | 9/2001 |
| CA | 2583519 A1 | 9/2001 |
| CA | 2583523 A1 | 9/2001 |
| CA | 2623698 A1 | 9/2001 |
| CA | 2597809 A1 | 2/2009 |
| CA | 2916490 A1 | 2/2013 |
| CA | 2852744 A1 | 4/2013 |
| CA | 2897043 A1 | 2/2016 |
| CA | 2893161 | 8/2019 |
| WO | 2014209854 A1 | 12/2014 |

OTHER PUBLICATIONS

Andrew McCauley, Sequence Stratigraphy, Depositional History, and Hydrocarbon Potential of the Mancos Shale, Uinta Basin, Utah (Year: 2013).*

* cited by examiner

APPARATUS, SYSTEMS, AND METHODS FOR ENHANCING HYDROCARBON EXTRACTION AND TECHNIQUES RELATED THERETO

CROSS-REFERENCE TO RELATED APPLICATION

This application claims the benefit of U.S. Provisional Patent Application 62/212,761 filed Sep. 1, 2015 entitled APPARATUS, SYSTEMS AND METHODS FOR ENHANCING HYDROCARBON EXTRACTION AND TECHNIQUES RELATED THERETO, the entirety of which is incorporated by reference herein.

FIELD OF THE INVENTION

The present application provides apparatus, systems, and methods for enhancing hydrocarbon extraction and techniques related thereto. More particularly, the present application provides techniques, which integrate spectroscopic data with other data about a surface mining region to enhance hydrocarbon extraction and recovery.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present invention. Accordingly, it should be understood that this section should be read in this light, and not necessarily as admissions of prior art.

Surface mining is useful in many industries and can typically be accomplished by removing mining material from the surface of a mining region and processing the removed mining material to extract hydrocarbons from the mining material. The processing of the mining material is subject to variations in the quality and properties of the mining material.

Conventional approaches involve different methods of estimating and/or measuring properties of the mining material. For example, the estimation may be performed by surveying the mining region or by obtaining informal measurements (e.g., observing color and/or adhesiveness) of certain samples of removed mining material. Also, a photo image may be used to visually determine brightness of the mining region. While these approaches may be performed in an efficient manner, the approaches do not provide accurate information about the properties of the mining material. Indeed, the approaches are subjective and depend upon the uncorroborated review by operations personnel.

Other approaches may involve more scientific rigor to provide more accurate analysis. For example, analytical ore characterization approaches may include wellbore analysis, which may include wire line log modeling, and/or core sampling and sample characterization (e.g., Dean Stark bitumen saturation, Methylene Blue Index (MBI), Grain size, Soluble Ions, or other core analysis techniques). While these approaches are used in advance of mining operations to estimate resource assessment and bitumen recoverability (e.g., extractability), these approaches are costly and time consuming. For example, wellbore drilling operations, which typically involve drilling wellbores spaced at about 100 meters apart, are expensive to perform and require long periods of time to complete the drilling and the associated analysis. While core analysis may be used to determine specific quality of the mining material and associated properties for a specific wellbore location, this approach is also expensive and time consuming as it typically needs to be performed each year over the operational lifetime of the mine. Further, the core data has to be interpolated laterally to cover the areas outside of the well, which may not properly represent the properties (e.g., fluvial depositional environments) between wells. Indeed, the geologic facies can change quite rapidly, which may result in errors in resource calculations. Also, certain samples may not be analyzed because they are perceived as bitumen lean sand zones (e.g., water wet or clay-rich) and clay zones. As a result, a certain amount of information is eliminated from the possible geologic data, which would be useful in building predictive models and/or aiding in the processing of the mining material.

Other approaches involve the use of spectroscopic data. For example, these approaches may involve using analyzers over a conveyor belt in the plant to provide a single point of information before the ore enters the processing equipment. The information can then be used by control room operators to adjust operation conditions in the processing plant to avoid plant upsets and/or sanding issues (e.g., sanding in the hydrotransport line). For example, U.S. Pat. No. 6,768,115 describes monitoring the degradation or oxidation of an oil sand ore feedstock by near infrared spectroscopy and then utilizing the information to control operating conditions in an oil sand processing plant. However, the limited timeframe hinders processing control flexibility in compensating for changes in the material being processed and does not provide an integrated mechanism to notify control room operators regarding changes in ore characteristics though the complete mining process. As a result, such approaches do not properly adjust for changes in the ore characteristics.

Other spectroscopic approaches describe relying upon specific and discrete wavelengths. See, e.g., U.S. Patent App. Pub. Nos. 2014/0326885, 2014/0347472, and 2012/0306257, and U.S. Pat. No. 4,433,239. However, by using only discrete wavelengths, the references fail to include additional information which may be used to lower uncertainty from the mining and extraction processes.

Thus, there remains a need in the industry for apparatus, methods, and systems that are more efficient and that can be utilized to enhance the hydrocarbon extraction operations. Also, a need exists to provide more flexibility in managing the mining materials in the various stages of the hydrocarbon extraction process and to lessen uncertainty about the mining material being processed in the hydrocarbon extraction process.

Other background references may include PCT Publication No. WO 2014/209854; U.S. Patent App. Pub. Nos. 2016/0033676; 2015/0337220; 2015/0323516; 2015/0068806; 2014/0208826; 2014/0197316; 2013/0327683; 2013/0169961 2011/0042143; 2010/0207018; and 2009/0071239; U.S. Pat. Nos. 9,087,338; 9,016,399; 8,857,915; 8,547,096; 8,336,370; 8,315,838; 8,117,891; 7,728,286; 7,718,956; 7,399,406; 7,369,229; 7,067,811; 6,929,330; 6,869,147; 6,554,368; 6,208,459; and 5,781,336; and Canadian Patent Application Publication Numbers CA 2916419 A1 and CA 2852744 A1.

SUMMARY OF THE INVENTION

In one or more embodiments, a method of performing a hydrocarbon extraction process having a plurality of hydrocarbon extraction stages is described. The method comprising: removing mining materials from a mining region as one of the plurality of hydrocarbon extraction stages; obtaining mine face spectroscopic data concurrently with removal of mining materials from a mine face associated with the mining region; performing one or more operations on the mining material removed from the mining region in a subsequent one of the plurality of hydrocarbon extraction stages; obtaining one or more stages of spectroscopic data concurrently with the performing of the one or more operations on the mining material; adjusting the one or more operations based on one of the mine face spectroscopic data, the stage spectroscopic data, and any combination thereof; and separating hydrocarbons from the mining materials after adjusting the one or more operations. The method further comprises performing a separation process in a primary separation cell unit to form a froth stream, a middling stream and a coarse tailings stream.

In one or more other embodiments, a system for hydrocarbon extraction is described. The system may include: extraction equipment, a mine face spectrometer, one or more stage spectrometers, a primary separation cell unit, and/or a control unit. The extraction equipment may be configured to remove mining materials from a mining region as one of a plurality of hydrocarbon extraction stages, while the mine face spectrometer may be configured to measure mine face spectroscopic data concurrently with removal of the mining materials by the extraction equipment. The one or more stage spectrometers may be configured to concurrently measure stage spectroscopic data with one or more of a plurality of operations performed on the mining material. The primary separation cell unit may be configured to receive the mining materials and to separate the mining materials into a froth stream comprising hydrocarbons, a middling stream and a coarse tailings stream. The control unit may be configured to communicate with one of the mine face spectrometer, one or more stage spectrometers, and any combination thereof and to provide one or more notifications for an adjustment to the plurality of operations based on the one of the mine face spectrometer, one or more stage spectrometers, and any combination thereof.

In certain embodiments, the spectroscopic data may include different wavelengths. For example, the spectroscopic data may include two or more of at least a portion of the ultraviolet spectral range, at least a portion of the visible spectral range and at least a portion of the infrared spectral range. As another example, the spectroscopic data may include at least a portion of the visible spectral range, at least a portion of near-infrared spectral range and at least a portion of the short-wavelength infrared spectral range. In yet another example, the spectroscopic data may include measured reflectance data for wavelengths in the range between 350 nanometers and 2500 nanometers.

In another embodiment, the method may integrate the mine spectroscopic data with other data. For example, the mine spectroscopic data may be integrated with mining data for the mining region, which may include heavy oil hand sample analysis data, well log data, core analysis data, ground penetrating radar data, and seismic data. This integrated data may be used to generate a stratigraphic framework and compute stacking patterns within the sequence stratigraphic framework based on the spectroscopic data. The method and system may also include integrating the one or more mining properties with a model of the mining region or hydrocarbon extraction stages.

Further, in other embodiments, the spectroscopic data may be adjusted against a standard reference and/or may be adjusted for environmental conditions. For example, the adjustments to one or more operations based on spectroscopic data may include: obtaining a reference standard associated with one of the mine face spectroscopic data and the stage spectroscopic data; comparing the reference standard with the one of the mine face spectroscopic data and the stage spectroscopic data to form refined spectroscopic data; determining one or more mining properties from the refined spectroscopic data; and using the one or more mining properties to adjust the one or more operations, wherein the mining properties may include one or more of mineralogy, bitumen saturation, bitumen viscosity, and grain size distribution. Also, the adjustments to one or more operations based on the spectroscopic data may include: determining environmental conditions associated with the one of the mine face spectroscopic data, the stage spectroscopic data, and any combination thereof; determining one or more adjustments to the one of the mine face spectroscopic data, the stage spectroscopic data, and any combination thereof based on the determined environmental conditions; and applying the one or more adjustments to the one of the mine face spectroscopic data, the stage spectroscopic data, and any combination thereof before adjusting the one or more operations based on the one of the mine face spectroscopic data, the stage spectroscopic data, and any combination thereof. The adjustments may include applying different weights to different portions of one of the mine face spectroscopic data, the stage spectroscopic data, and any combination thereof based on the environmental conditions.

BRIEF DESCRIPTION OF THE FIGURES

The foregoing and other advantages of the present disclosure may become apparent upon reviewing the following detailed description and drawings of non-limiting examples of embodiments.

DETAILED DESCRIPTION OF THE INVENTION

Figure 1:
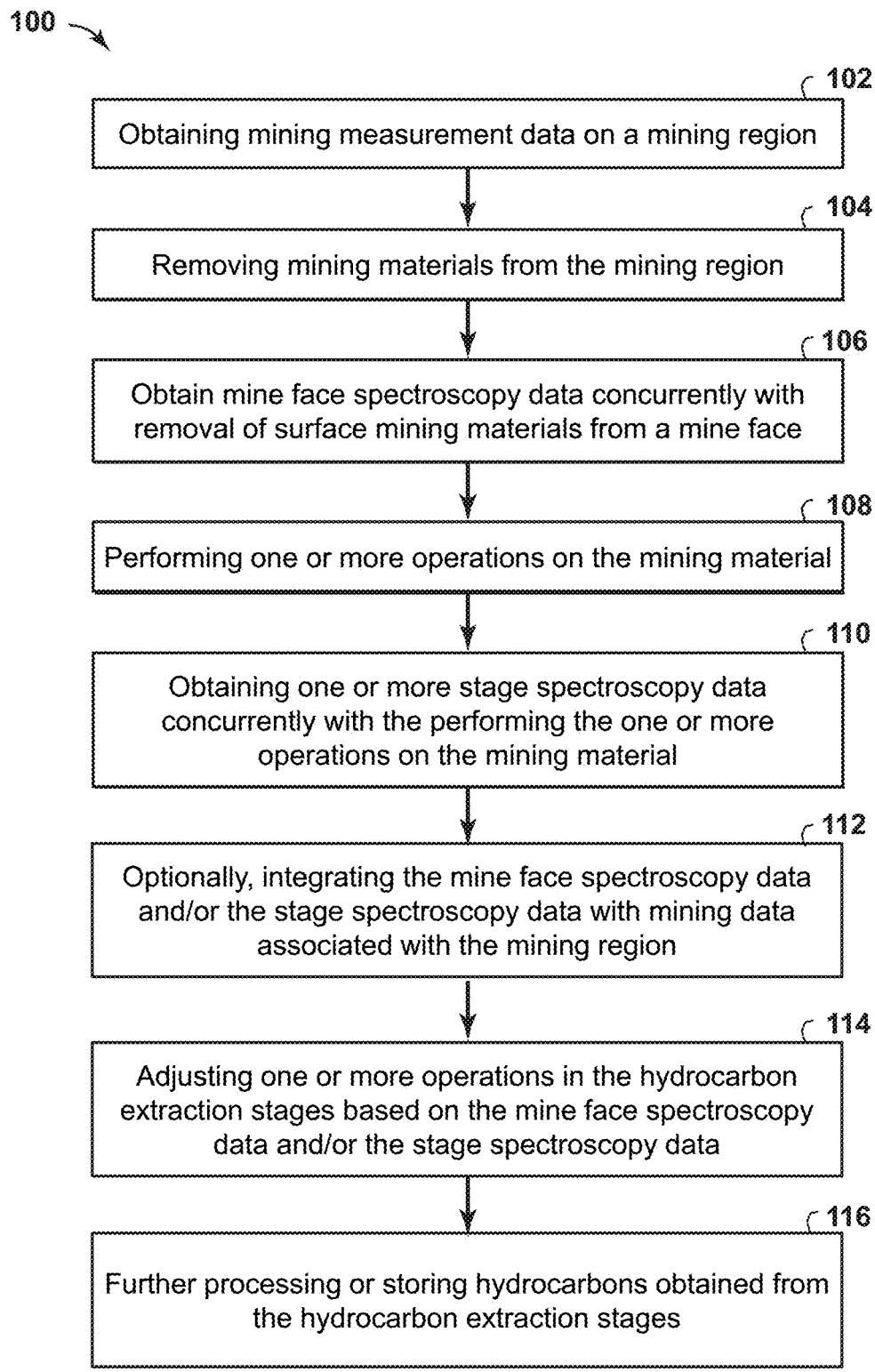
FIG. 1 is a flow diagram of an exemplary method of adjusting operations in one or more hydrocarbon extraction stages based on spectroscopic data.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, fewer than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

Unless otherwise explained, all technical and scientific terms used herein have the same meaning as commonly understood by one of ordinary skill in the art to which this disclosure pertains. The singular terms "a", "an", and "the" include plural referents unless the context clearly indicates otherwise. Similarly, the word "or" is intended to include "and" unless the context clearly indicates otherwise. The term "includes" means "comprises." All patents and publications mentioned herein are incorporated by reference in their entirety, unless otherwise indicated. In case of conflict as to the meaning of a term or phrase, the present specification, including explanations of terms, control. Directional terms, such as "upper", "lower", "top", "bottom", "front", "back", "vertical", and "horizontal" are used herein to express and clarify the relationship among various elements. It should be understood that such terms do not denote absolute orientation (e.g., a "vertical" component can become horizontal by rotating the device). The materials, methods, and examples recited herein are illustrative only and not intended to be limiting.

Persons skilled in the technical field will readily recognize that in practical applications of the disclosed methodology, it is partially performed on a computer, typically a suitably programmed digital computer. Further, some portions of the detailed descriptions which follow are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "processing" or "computing", "calculating", "determining", "displaying", "copying", "producing", "storing", "adding", "applying", "executing", "maintaining", "updating", "creating", "constructing", "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

As used herein, "concurrently" means happening, performing, or occurring at time periods that overlap or are within a time interval with respect to each other. For example, if a first operation is being performed during a first time period and a second operation is being performed during a second time period, the operations are performed concurrently with respect to each other if the first time period and second time period overlap or the first time period and the second time period are performed within a specific time interval (e.g., within a specific period of time, such as thirty minutes, sixty minutes, or ninety minute), or within the same operation stage of a process. For example, if spectroscopic data are collected from a mine face and mining material is removed from the mine face, the operations are concurrently performed for the material removal stage. Similarly, if spectroscopic data are collected from mining material during a processing stage and the mining material is being processed in that processing stage, these operations are concurrently performed for the processing stage. Likewise, spectroscopic data measurements that are made at the same time as the sampling operations are taken in "concurrently", as compared to measurements that are made in a lab on samples that were previously collected. Likewise, if spectroscopic data are collected from mining material on the apron feeder and adjustments are made to the separation stage, the adjustments are made concurrently if they are made within fifteen minutes, or within thirty minutes, or within sixty minutes, or within ninety minutes of the measurement of the spectroscopic data.

As used herein, "real-time" means happening, performing, or occurring at the same or substantially same time. Thus, "real-time" is a subset of "concurrent", such that operations that occur in real-time are also occurring concurrently. For example, if a first operation is being performed during a first time period and a second operation is being performed during a second time period, the operations are performed in real-time with respect to each other if the first time period and second time period are substantially the same time periods.

The present techniques relate to systems and methods for enhancing hydrocarbon extraction and recovery and techniques related thereto. In particular, the present techniques involve obtaining measurement data, such as spectroscopic data or gamma ray data, integrating the measured data with other information about a mining region, and using the measured data to enhance hydrocarbon recovery. For example, the measured data may be integrated at various stages in the hydrocarbon extraction process, such as the mining stage or the processing stage. The present techniques enhance ore characterization by providing a method and system, which may be performed concurrently or in real-time, to perform ore analysis from mining regions (e.g., surface or near surface regions). The present techniques characterize mining material (e.g., ore samples, ore core, ore piles, ore bodies, ore faces, or ore dumped into hoppers) to provide mining properties, which are used in managing operations in the hydrocarbon extraction process. The mining properties may include one or more of: bitumen saturation; clay content; water saturation; mineralogy (e.g., type and/or abundance); mean grain size; grain size distribution; waste components (e.g., problematic materials in extractability, such as coal and/or organic-rich solids); percent fines; and/or bitumen characteristics (e.g., biodegradation, weathering, and/or viscosity). As a result, the present techniques provide a mechanism to: (1) correlate concurrent or real-time mining properties with concurrent or real-time processing results (e.g., correlate ore characteristic data with extractability performance); (2) increase processing agility by increasing notification time and stage status to adjust operations in the method (e.g., change process variables to lessen issues, such as fouling or other negative events, or to provide improved separation of ore from the mining material); and/or (3) enhance decision making and adjustments to the process. This mechanism may be automated or may be used by personnel, such as processing geologists and control room operators associated with the hydrocarbon extraction process, to further enhance the process.

Embodiments of the present techniques may be utilized at various stages of the hydrocarbon extraction process. Detectors, such as spectrometers or gamma ray detectors, may be used at various hydrocarbon extraction stages to collect energy reflected from objects (e.g., electromagnetic energy reflected from samples or mining material) or to collect energy naturally emanated from the mining material (e.g., gamma rays). For example, spectrometers may be mounted on various equipment components at various stages to passively collect energy reflected from the mining material, such as sunlight reflected from the mining material. As another example, gamma ray detectors may be mounted on various equipment components at various stages to passively collect energy emitted from the mining material. The detectors may be mounted, for example mining machines and equipment, or may be portable (e.g., handheld or detectors disposed on a tripod). The measured data may be used to provide ore grade information about mining material at various stages in the process. Additionally, data from different stages of the hydrocarbon extraction process may be integrated together to provide more information about the mining material being directed through the process and to provide personnel with time to perform adjustments to the operations in the various stages. For example, spectroscopic data may be used to enhance processing by providing a mechanism to enhance ore-waste decisions at the mine face, to enhance blending decisions at feedstock piles, to enhance operational efficiency by integrating data at the different stages, to lessen fouling or shut down risks, and to provide real-time data or concurrent data to enhance production intelligence and models (e.g., reservoir models or geologic models). In particular, for oil sands processing operations, the present techniques provides a mechanism to characterize materials during various mining stages to enhance decision making concurrently with the processing of the mining material (e.g., extracted ore).

The measured data may include spectral information from one or more wavelength intervals. For example, the measured data may include energy from the gamma ray spectral range (e.g., 0.0001 nanometers (nm) to 0.01 nm), x-ray spectral range (e.g., 0.01 nm to 10 nm), ultraviolet spectral range (e.g., 10 nm to 380 nm), visible spectral range (e.g., 380 nm to 750 nm), and/or infrared spectral range (e.g., 750 nm to 1 millimeter (mm)). The infrared spectral range may include the near-infrared spectral range (e.g., 750 nm to 1.4 micrometers ($\mu$m)), short-wavelength infrared spectral range (e.g., 1.4 $\mu$m to 3 $\mu$m), mid-wavelength infrared spectral range (e.g., 3 $\mu$m to 8 $\mu$m), long-wavelength infrared spectral range (e.g., 8 $\mu$m to 15 $\mu$m) and far-infrared spectral range (e.g., 15 $\mu$m to 1 mm). In preferred embodiments, the detectors may be such that they are apple of measuring data in the spectral range of 350 nm to 2500 nm.

To collect the energy, the detectors may include cameras for two-dimensional (2D) or three-dimensional (3D) data capture of energy from all parts or discrete parts of the electromagnetic spectrum (e.g., gamma rays to x-rays to ultra violet to visible to near-infrared to short-wavelength infrared to mid-wavelength infrared to long-wavelength infrared to far-infrared). The detectors may be configured to measure energy reflected (e.g., visible light or short-wavelength infrared) or emitted (e.g., long-wavelength infrared) from the mining material. Further, other energy emanating naturally or unnaturally from mining material (e.g., gamma rays and/or long-wavelength infrared) may also be collected. The measured data may be obtained by using passive illumination (e.g., reflectance obtained using the sun as the energy source) or using active illumination (e.g., reflectance obtained using activity energy sources such as broad spectrum lights and/or lasers). For active illumination, the illumination source may be mounted on equipment near the detector (e.g., on the shovel and/or mounted above a hopper for the ore crusher) or be contained within the detector (e.g., in portable tools the illumination source may be sourced internally, such as lasers) and may be configured to direct the energy toward the mining material.

Accordingly, in one or more embodiments, the measured data may include different wavelength intervals. For example, the measured data may include two or more of at least a portion of the ultraviolet spectral range, at least a portion of the visible spectral range and at least a portion of the infrared spectral range. In another example, the measured data may comprise at least a portion of the visible spectral range, at least a portion of near-infrared spectral range, and at least a portion of the short-wavelength infrared spectral range. In yet another example, the measured data may comprise measured reflectance data for wavelengths from 350 nanometers to 2500 nanometers, such as spectroscopic data for wavelengths from 350 nanometers to 2500 nanometers.

To manage the measured data, a control unit may be utilized to communicate with one or more of the detectors. The control unit may be a processor, computer system or other processing device that integrates the measured data from the various detectors. The integration of the measured data may include updating a model of the mine, mining region or process, and/or updating one or more properties along with an associated location along the various stages of the hydrocarbon extraction process. For example, in certain embodiments, spectroscopic data may be an average signature from a spot size or a pixelated image, which range from millimeters to ten or more meters in size. To form the signature, several measurements (e.g., two or more, or ten or more) may be averaged together to form an average measurement for a spot or pixel(s).

In one or more embodiments, the measured data may be adjusted or calibrated to further enhance the hydrocarbon extraction process. For example, the measured data may be processed with a filter to remove environmental noise. The filter may comprise measured data collected at another time from a reference standard. The reference standard data may be obtained prior to the measured spectroscopic data, after the measured spectroscopic data, and/or any combination thereof. Further, the obtaining of the reference standard may be within a set period of time relative to the acquisition of the measured spectroscopic data (e.g., within the ten seconds, or within sixty seconds, or within fifteen minutes, or within one hour, of acquiring the measurement data, or may be within the one day or within one week of acquiring the measurement data and/or within the one week of acquiring the measurement data). The reference standard may be a surface that is white or black, for example. Thus, the measured data (e.g., reflectance data) may be calibrated against the reference standard (e.g., reflectance standard, which may be about 100% reflective). Further, the measured data may be adjusted based on environmental conditions. The adjustments to the measured data may include weighting the measured data from different wavelengths with different weights based on the environmental conditions. The environmental conditions may include light level (e.g., amount of sunshine), amount of rain, amount of snow, amount of fog, amount of ice, temperature range, and the like.

In certain embodiments, other features may be used to further enhance the hydrocarbon extraction process. For example, the spectral data (e.g., peak position, intensity, shape, breadth, etc.) from all parts or discrete parts of the received spectrum may be calibrated to lab measurements of ore or mining material (e.g., ground-truthing data) and may be used as a "training" or reference set of measurements. Lab measurements may include x-ray diffraction ("XRD") responses, spectral gamma-ray ("SGR") responses, x-ray fluorescence ("XRF") responses, Dean Stark bitumen percentages, grain sizes, total extractable organic matter ("TEOM") responses, total organic carbon ("TOC") responses, whole gas chromatography ("GC") responses, bitumen molecular weight responses (e.g., SIMDIST measurements), bitumen liquid chromatography responses (e.g., saturates, aromatics, resins, and asphaltenes ("SARA") measurements), and/or bitumen viscosity responses. Further, the spectral data and/or ground-truthing data may be used to construct chemometric models (e.g., mathematical and/or statistical models). Chemometric models may be used to understand and to estimate unknown samples in the mine or mining materials. Values for unknowns may be estimated from known relationships between spectral responses (e.g., due to physical and chemical properties of the mining material) and ground-truthing data in the training data. Also, the chemometric model may be processed to produce an output number for an average spot or pixel(s) or a false-color pixelated image, which may be based on the correlation between known "training" data and unknown samples. The outputs from chemometric models that represent average properties over a spot and/or pixel(s) may be represented numerically and may be produced concurrently or in real-time to mining operators (e.g., personnel). The outputs of multi-pixel images may be represented in false color images and may require post-processing. Further, the 2D false color images may be exported in 3D visualization software, which may include interpolating data to form 3D interpretation models of the rock facies, stratigraphic models, and predictive models.

Further, in one or more embodiments, the measured data may be integrated with mining data to enhance the operations. For example, the spectroscopic data may be integrated with mining data, such as heavy oil hand sample analysis data, well log data, core analysis data, ground penetrating radar data, seismic data and outcrop, and/or mine face analysis data. The additional mining data may be used to verify or further determine the various mining properties (e.g., mineralogy, bitumen saturation, bitumen viscosity, and grain size distribution in the mining environment). Also, the spectrometry technology may enhance inter-well correlations if it can be applied at a lithofacies scale to capture stacking patterns within a sequence stratigraphic framework.

Moreover, in one or more embodiments, the detectors may be portable, secured to equipment, or any combination thereof. For example, two or more portable spectrometers may be used to obtain data about mining properties (e.g., ore characteristics) from direct scans of the mine face and/or removed mining material (e.g., bitumen ore), which may be in stockpiles or being transported along the stages of the process. In another example, the two or more fixed spectrometers, which are used to obtain data, may include a first spectrometer attached to the excavation equipment to provide data on the mine face and/or a second spectrometer attached to a dump truck or conveyer belt to provide data on the mining material (e.g., bitumen ore), which may be in stockpiles or may be transported along one of the stages of the process. Also, a combination of portable and fixed detectors may be used. In particular, the system may include a first fixed spectrometer attached to the excavation equipment, a second fixed spectrometer attached to a dump truck, and a third portable spectrometer that may be used on stockpiles or along the conveyer belt. In each of these configurations, the detectors may communicate with each other and/or a control unit (e.g., processor or computer system) that is utilized to manage the measured data from the respective detectors.

In one or more embodiments, the method and system of the present techniques may include handheld and/or portable detectors (e.g., FTIR—Fourier-Transform Infrared device) point measurement on hand samples. For example, the method may involve providing at least one portable spectrometer (e.g., sensing device); scanning individual mining material of minerals and bitumen (e.g., end members) from a mine to build inorganic and/or organic spectral response library (e.g., location of spectral response for each mining material scanned); capturing spectroscopic data (e.g., to build semi-quantitative models); determining mineral and bitumen quantity (e.g., using area under the peak of spectral response); managing the flow of extracted mining material, such as ore; building regression lines to calculate semi-quantitative mineral and bitumen quantity from spectral response of mining material and/or samples (e.g., mixed minerals and bitumen); performing ground truth predictive models against known samples; and taking measurements with portable spectrometer on unknown hand samples in the mine during routine mine rounds to determine mineralogy and bitumen characteristics (e.g., using predictive models or other information).

Further still, in other embodiments, the method and system of the present techniques may include mine face spectrometry, which may be wide area measurements from hand sample to outcrop scale. This method and system may include scanning mining materials (e.g., individual minerals and bitumen, such as end-members) to build inorganic and/or organic spectral response library (e.g., location of spectral response for each items scanned); capturing data in core and outcrop to build semi-quantitative models for mineral and bitumen quantity and distribution using spectral response; developing computer post-processing of pixels (e.g., averaged areas) from core and outcrop data captured to produce false color image of core or outcrop according to mineralogy or bitumen characteristics; scanning the mine face to measure spectral response of mine face during mine rounds (e.g., measured spectroscopic data) to capture 2D panels of passive energy received from the mine-face; post-processing the measured spectroscopic data to create false-color images in 2D panels for mineralogy and bitumen characteristics; integrating with photographs (e.g., high resolution photographs of mine face); and populating modeling software or other data integration software to correlation with the stratigraphy.

Beneficially, the present techniques provide various enhancement to the hydrocarbon extraction process. One enhancement is providing a mechanism to measure mining properties (e.g., ore characteristic controls on extractability) and in real-time or concurrently to adjust mining operations (e.g., mining activities in the different stages and/or blending). This provides increased notification to operations personnel (e.g., increases the agility of control room personnel), which may increase efficiency in the process, and may lessen down time. In addition, the present techniques may be used to manage the feed rate and resource mass balance to provide enhanced operation. The spectroscopic data may be used to lessen core analysis, which results in a lessening of costs, and to increase inter-well coverage for bitumen saturation (e.g., enhance the resource mass balance for the process). Also, the use of the measured spectroscopic data may be used to develop learnings and enhance calibration of other systems, such as calibrating core descriptions to well ties (i.e., the area between wells), which may lessen the need for additional wells. Further, the measured spectroscopic data may be used to identify and to determine the cause of the problematic event, such as upsets that may occur in the processing plant. This identification and determination may increase the ability to avoid future upsets (e.g., provide production intelligence), which may further lessen down time. The present methods and techniques may be further understood with reference to FIGS. 1 to 10, which are described further below.

FIG. 1 is a flow diagram 100 of an exemplary method of performing hydrocarbon extraction stages with measured data. In this method, spectroscopic monitoring is performed at two or more hydrocarbon extraction stages in a hydrocarbon extraction process. The measured spectroscopic data may be utilized to provide operations personnel with information concurrently or in real-time with the performance of the various stages. The spectroscopic data from the two or more locations provide information about the mining material throughout the process, which may be performed concurrently or in real-time. The measurements may be performed in concurrent analysis, which may be performed in a continuous or periodic manner (e.g., at set periods of time, such as every second, every 10 seconds, or every minute for example).

In this diagram 100, measurement mining data on a mining region may be obtained, as shown in block 102. The measurement data may include ground penetrating radar, seismic data, well log data, or the like. At block 104, mining materials are removed from the mining region. The removal of the mining materials may include excavating with excavation equipment, such as heavy earth moving equipment, excavators, backhoes, and the like. At block 106, mine face spectroscopic data are obtained concurrently with removal of surface mining materials from a mine face. The mine face spectroscopic data may be obtained prior to the removal of the mining materials, during the removal of the mining material, or after removal of the mining material, but before transporting the mining material. The spectrometer may be one or more fixed spectrometers secured to the excavation equipment and/or one or more portable spectrometers. The spectroscopic data may be used to provide properties, which are used to: calculate in-place bitumen; predict extractability, slurry rheology, and/or chemistry; maximize recovery; and/or avoid processing plant upsets.

At block 108, one or more operations on the mining material may be performed.

The one or more operations may include transporting the mining material, storing the mining material, and/or processing the mining material to separate hydrocarbons from the other material. Exemplary operations are described further below in FIG. 2.

At block 110, at one or more stages spectroscopic data may be obtained concurrently with the performing of the one or more operations on the mining material. The stage spectroscopic data may be obtained and communicated to a control unit from different operations to provide further information about the processing of the mining material.

Then, in block 112, the mine face spectroscopic data and/or the stage spectroscopic data may optionally be integrated with mining data associated with the mining region. This integration may be used to validate or verify mining properties. For example, the spectroscopic data may be integrated with mining data, such as heavy oil hand sample analysis data, well log data, core analysis data, ground penetrating radar data, seismic data and outcrop and/or mine face analysis data. The additional data may be used to verify or further determine the various mining properties (e.g., mineralogy, bitumen saturation, bitumen viscosity, and grain size distribution in the mining environment). Further, if the integrated information can be applied at a lithofacies scale, the integration may be used to enhance inter-well correlations and to capture stacking patterns within a sequence stratigraphic framework.

At block 114, one or more operations are adjusted in the hydrocarbon extraction stages based on the mine face spectroscopic data and/or the stage spectroscopic data. The adjustments may include adjusting one or more of the process water quality, process aids, feed rates of solvents, water and/or mining material, dilution and/or dispatch schedule. At block 116, the hydrocarbons obtained from the hydrocarbon extraction stages are further processed and/or stored.

Beneficially, the present techniques may lessen the need for coring operations as compared to conventional approaches, and thus also the need for roads and other infrastructure to access coring locations, lessen maintenance or storage of frozen cores, and/or lessen the need for analysis on core samples (e.g., Dean Stark bitumen saturation, Methylene Blue Index (MBI), grain size, and Soluble Ions, and the like). Further, as data are interpolated laterally, the use of the present techniques can decrease the frequency (in space and in time) of coring operations. For example, the data can be used to interpolate between coring operations, such that coring operations can be spaced further apart, such as greater than 100 meters apart, or greater than 150 meters apart, or greater than 200 meters apart.

Beneficially, the present techniques may also lessen process upsets as compared to conventional approaches. For example, the more continuous updating of spectroscopic data may be used to address rapid changing of the geologic facies due to fluvial depositional environments. This may lessen unplanned process upsets such as those due to bitumen saturation changes, waste intervals, and ore chemical changes, which lessen operational efficiency (e.g., introduce errors in resource calculations, mining plans, blending plans, and ore recovery).

Moreover, conventional techniques may not analyze all core samples that are obtained because of the length of time required for analysis of the different zones. That is, bitumen lean sand zones (e.g., water wet or clay-rich) and clay zones are not typically analyzed, as the focus is on the bitumen-rich ore zones. Thus, the conventional approach often eliminates valuable information from the geologic information needed to properly build predictive models. The use of fewer core wells provides additional time for more comprehensive analysis of cores, which enhances the spatial predictability. Further still, the concurrent monitoring with spectroscopic data enhances the time period for notification about mining properties (e.g., ore characteristics) to the processing plant control room. For example, measuring mining properties on the mine face may provide at least one hour of notification time.

In addition, the use of spectroscopic data may enhance the forensic (or backward looking) analysis for the plant. The present techniques provide a mechanism to obtain and average mining properties (e.g., ore characteristic data), which may also be correlated with average extractability performance in the plant to enhance production intelligence (e.g., learnings associated with ore characteristics that cause plant upsets, fouling or decrease in extractability). As spectroscopic data is obtained at various stages in the process, connecting mining properties to performance in the plant may be used to enhance long term extractability averages. Therefore, the use of the mine face spectroscopic data and stage spectroscopic data can provide a method for forensic feedback when investigating process upsets. That is, after a process upset occurs, analysis of the data can provide production intelligence to aid in determining the cause of the upset.

Figure 2:
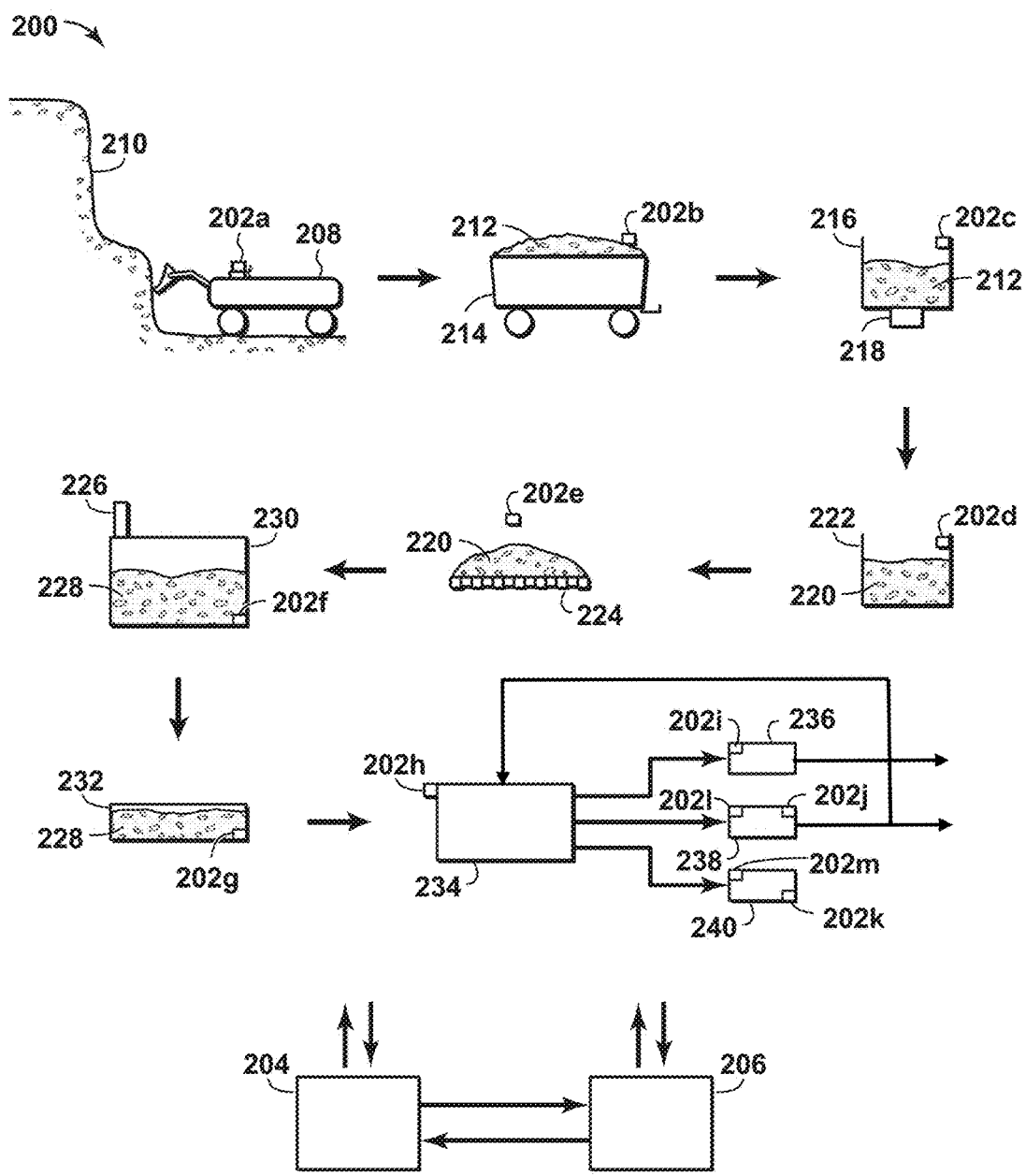
FIG. 2 is an exemplary diagram of a system for hydrocarbon extraction using spectroscopy monitoring.

FIG. 2 is an exemplary diagram of a system for hydrocarbon extraction using reflectance monitoring, such as spectroscopic and/or gamma ray monitoring, in accordance with an exemplary embodiment of the present techniques. In this diagram, the system 200 may include various stages from an exemplary hydrocarbon extraction process. The system 200 may include various detectors 202a to 202m, which are utilized to obtain measured data and communicate with a control unit 204. The control unit 204 may be configured to interact with the process control center 206, which adjusts or manages the operations being performed in the various hydrocarbon extraction stages of the hydrocarbon extraction process. The detectors 202a to 202m may be fixed or portable and may be configured to obtain electromagnetic spectrum, such as one or more of gamma rays spectrum, x-rays spectrum, ultra violet spectrum, visible spectrum, near-infrared spectrum, short-wavelength infrared spectrum, mid-wavelength infrared spectrum, long-wavelength infrared spectrum, far-infrared spectrum and any combination thereof.

In this system 200, extraction equipment 208 is utilized to remove mining material from the mine face 210. The extraction equipment 208 may include shovels, augers, excavators, bulldozers, or other suitable equipment. Further, a detector 202a may be associated with the extraction equipment 208. The detector may be a spectrometer 202a that is configured to obtain mining spectroscopic data and transmit the mining spectroscopic data to the control unit 204. In this manner, the control unit 204 may process the mining spectroscopic data concurrently with the removal of the mining material.

Once the mining material is removed from the mine face 210, the removed mining material 212 may be transported via earth moving equipment 214. The earth moving equipment 214 may include dump trucks, backhoes, pickup trucks, sleds, or other suitable devices. A transport detector, such as transport spectrometer 202b, may be associated with the earth moving equipment 214 and/or may be positioned at different locations along the transport path. The transport spectrometer 202b may be configured to obtain transport spectroscopic data and transmit the transport spectroscopic data to the control unit 204. In this manner, the control unit 204 may process the transport spectroscopic data concurrently with the transport of the removed mining material.

Then, the mining material 212 is provided to a hopper 216, which may also include ore crushing equipment 218. The hopper 216 may be a container configured to funnel mining material to a crusher, while the ore crushing equipment 218 may include spinning jaws or wheels. A detector, such as hopper spectrometer 202c, may be associated with the hopper 216 and/or ore crushing equipment 218. The hopper spectrometer 202c may be configured to obtain hopper spectroscopic data and to transmit the hopper spectroscopic data to the control unit 204. In this manner, the control unit 204 may process the hopper spectroscopic data concurrently with the processing of the mining material in the hopper 216 and/or after being crushed.

Once crushed, the crushed mining material 220 is provided to a surge bin 222. A conveyor (not shown) may be used to provide the crushed mining material from the crushing equipment 218 to the surge bin 222. Along the path of the conveyor there may be one or more detectors, such as spectrometers, configured to obtain spectroscopic data. The conveyor spectrometer(s) may transmit the conveyor spectroscopic data to the control unit 204. In this manner, the control unit 204 may process the conveyor spectroscopic data concurrently with the moving of the mining material along the conveyor and, for example, may be used to adjust the speed of conveyance as needed.

The surge bin 222 may include a container configured to provide the mining material at a certain flow rate for a specific amount of time. A spectrometer, such as surge bin spectrometer 202d, may be associated with the surge bin 222. The surge bin spectrometer 202d may be configured to obtain surge bin spectroscopic data and to transmit the surge bin spectroscopic data to the control unit 204. In this manner, the control unit 204 may process the surge bin spectroscopic data concurrently with the processing of the mining material 220 in the surge bin 222.

From the surge bin 222, the mining material 220 is provided to a conveyor 224. The conveyor 224 may include a moving mat or the like. A detector, such as conveyor spectrometer 202e, may be associated with the conveyor 224. The conveyor spectrometer 202e may be configured to obtain conveyor spectroscopic data and to transmit the conveyor spectroscopic data to the control unit 204. In this manner, the control unit 204 may process the conveyor spectroscopic data concurrently with the movement of the mining material 220 along the conveyor's path.

From the conveyor 224, the mining material is mixed with a liquid via a liquid inlet 226 to form a slurry 228 of mining material in a mixing unit 230. The mixing unit 230 may include a container and mixing element configured to mix the liquid and the mining material. The liquid may be solvent, water, and/or a caustic solution, for example. Further, the container may be pressurized to enhance the mixing of the liquid and the mining material. A detector, such as a mixing spectrometer 202f, may be associated with the mixing unit 230. The mixing spectrometer 202f may be configured to obtain mixing spectroscopic data and to transmit the mixing spectroscopic data to the control unit 204. In this manner, the control unit 204 may process the mixing spectroscopic data concurrently with the mixing of the mining material with the liquid. Further, the mixing spectroscopic data may be utilized to control the liquid inlet valve 226, and, for example, may be used to control the amount of caustic that is introduced to the mixing unit 230. Likewise, the conveyor spectroscopic data may be utilized the liquid inlet valve 226, and, for example, be used to control the amount of caustic that is introduced to the mixing unit 230. Further, the conveyor spectroscopic data from the conveyor spectrometer 202e may be integrated with the mixing spectroscopic data from the mixing spectrometer 202f to improve the control of the amount of each type of fluid (e.g., solvent, water, and/or caustic) mixed with the mining material to provide optimized hydrocarbon recovery.

From the mixing unit 230, the slurry 228 of mining material is conveyed through a conduit equipment 232. The conduit equipment 232 may include tubular members, pumps, valves, and other equipment. A detector, such as a conduit spectrometer 202g, may be associated with the conduit equipment 232. The conduit spectrometer 202g may be configured to obtain conduit spectroscopic data and to transmit the conduit spectroscopic data to the control unit 204. In this manner, the control unit 204 may process the conduit spectroscopic data concurrently with the movement of the slurry through the conduit equipment 232.

Then, the slurry may be subject to a separation process in a primary separation cell unit 234. The primary separation cell unit 234 may include a separation vessel configured to separate the slurry into froth 236, middling 238, and coarse tailings 240. The froth may include some hydrocarbons, along with some solids and organic material. The tailings may include sand, rock, and lesser amounts of hydrocarbons. The middlings may include hydrocarbons, solids, organic material, sand, and rock. A detector, such as a separation spectrometer 202h, may be associated with the primary separation cell unit 234. One or more detectors, such as froth spectrometer 202i, middling spectrometers 202l and 202j, and coarse spectrometers 202m and 202k may be associated with the respective streams from the primary separation cell unit 234. The separation spectrometer 202h, froth spectrometer 202i, middling spectrometers 202l and 202j, and coarse spectrometers 202m and 202k may be configured to obtain separation spectroscopic data and to transmit the separation spectroscopic data to the control unit 204. In this manner, the control unit 204 may process the separation spectroscopic data, along with the spectroscopic data for the respective separated streams, concurrently with the separation of the slurry of mining material through the primary separation cell unit 234.

The control unit 204 may be utilized as a central location to manage the various detectors utilized in the various hydrocarbon extraction stages, such as one or more of the spectrometers 202a to 202m. The control unit 204 may include power modules, communication modules, and/or management modules. The control unit 204 may be disposed in the control room 206 and/or disposed near the control room 206 to facilitate communication and interaction with the equipment in the control room 206 and/or operators in the control room 206. Also, other embodiments may include the control unit 204 being located at a remote location and configured to facilitate communication and interaction with the equipment in the control room 206 and/or operators in the control room 206.

The control unit 204 may include management modules, which may include hardware, sets of instructions stored in memory and configured to be accessed by a processor to execute the set of instructions, or a combination of both. These modules may include display and imaging modules that present the images or visible indications to an operator, and modules configured to determine the properties of the mining material at the different stages of the process. Further, the modules may include a communication module configured to communication with other equipment. The communication module may include one or more antenna to communicate with one or more of spectrometers and/or control room equipment. The communication equipment may utilize technologies, such as radio, cellular, wireless, microwave, or satellite communication hardware and software. Also, the control unit 204 may utilize Ethernet communications, such as local area networks or wide area networks.

The control room 206 may be utilized as a central location to manage one or more of the stages in the process. The control room 206 may include various monitoring modules (e.g., equipment to manage the equipment in the process) and/or communication modules (e.g., equipment to communicate with the managed equipment and the control unit 204). The monitoring module may include equipment to manage the extraction equipment 208, earth moving equipment 214, hopper 216, ore crushing equipment 218, surge bin 222, conveyor 224, fluid inlet 226, mixing unit 230, conduit equipment 232, and/or primary separation cell unit 234, for example. The communication modules may include one or more antenna to communicate with one or more of the equipment, one or more of the spectrometers 202a to 202m and/or control unit 204.

The type of detector used at any particular stage, i.e., spectrometer or gamma ray detector, may depend on the type of material being tested at that stage. For example, when the material being tested comprises liquids moving through a pipeline, a gamma ray detector may be preferred. Thus, in some embodiments, spectrometer detects may be preferred at the mine face (e.g., 202a), in/on earthmoving equipment (e.g., 202b), in hoppers (e.g. 202c), on/over conveyor belts (e.g., 202e), while gamma ray detectors may be preferred in mixing equipment (e.g., 202f) or fluid conduit equipment (e.g., 202g).

As an example, the one or more operations in the hydrocarbon extraction stages may be adjusted based on the mine face spectroscopic data and/or other stage spectroscopic data (e.g., block 114 of FIG. 1). The spectroscopic data, which may be processed in a control unit (e.g., control unit 204 of FIG. 2), may be processed to determine the respective mining properties for the mining material at that stage.

For example, the mine face spectroscopic data from the mine face spectrometer 202a may be utilized to direct the mining equipment 208. Thus, for example, the data can be used adjust where the mining material is removed from the mine face 210 in order to obtain a better mixture of mined material and/or to avoid bitumen-lean zones of the mine face.

As another example, the conveyor spectroscopic data from the conveyor spectrometer 202e and/or the mixing spectroscopic data from the mixing spectrometer 202f can be used to control the liquid inlet valve 226 and adjust the amount and/or type of liquid (e.g., water, solvent, and/or caustic) that is being introduced into the mixing equipment 230. For example, the amount of caustic being used can be adjusted to account for differences in the amount of bitumen and/or ore detected by the conveyor spectrometer 202e.

As a further example, data from the froth spectrometer 202i and/or the middling spectrometers 202l and/or 202j can be used to detect the amount of hydrocarbons, sands, and/or rock in the froth and middlings and be used to return at least a portion of the forth and/or middlings to the separation unit 234 for improved separation.

To further enhance the process, the processing of the spectroscopic data may include using a filter to lessen noise in the spectroscopic data. The filter may include a standard reference based on spectroscopic data, which may be collected at another time against a basis (i.e., reference) object. The basis object may be a surface that is white or black, for example. For example, the measured data, which may be reflectance data, may be calibrated against a reference standard, such as a reflectance standard of about 100% reflectance.

Figure 3:
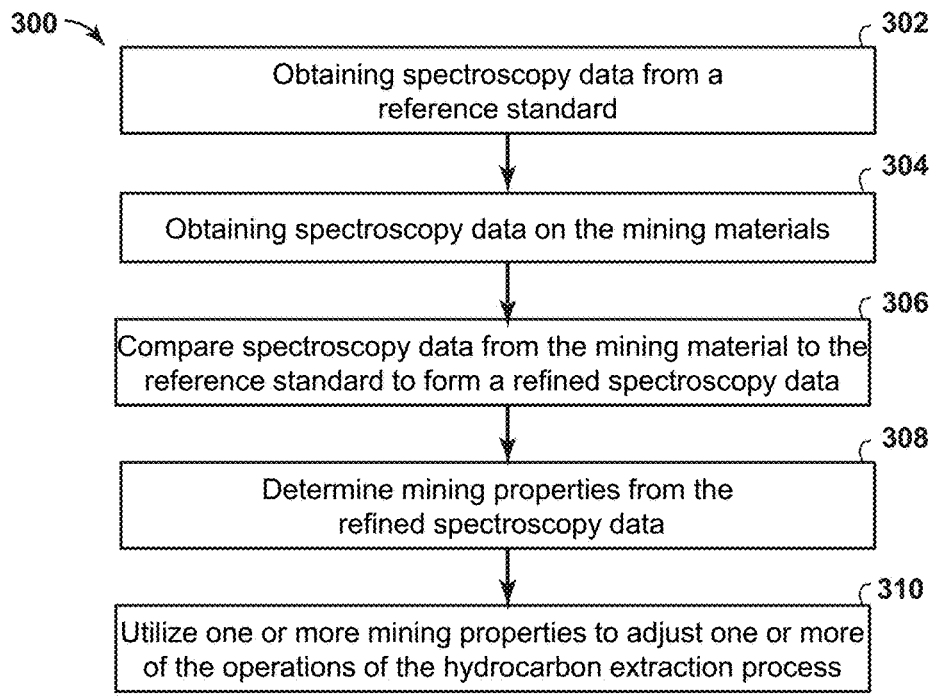
FIG. 3 is a flow diagram of an exemplary method of analyzing measured spectroscopic data in a hydrocarbon extraction process.

As an example, FIG. 3 is a flow diagram 300 of an exemplary method of analyzing the spectroscopic data in a hydrocarbon extraction process in accordance with an exemplary embodiment of the present techniques. In this method, the spectroscopic data are from one or more of the hydrocarbon extraction stages in the hydrocarbon extraction process is analyzed to determine mining properties of the mined material. Thus, the spectroscopic data are utilized to provide information about the mining properties concurrently with the performance of the various stages in the hydrocarbon extraction process. The processing of the spectroscopic data may be performed in one or more of the spectrometers and/or a control unit. Further, as shown in diagram 300, the spectroscopic data from one or more of the hydrocarbon extraction and recovery stages may be calibrated against a reference standard (e.g., from a basis object) to provide improved analysis of the data.

In this diagram 300, spectroscopic data from a reference standard for calibration may be obtained, as shown in block 302. The spectroscopic data from the reference standard for calibration may be obtained by measuring spectroscopic data for a calibration at the same location and with the same equipment as the spectroscopic data associated with the mining material and/or may be a previously determined reference standard. At block 304, spectroscopic data are obtained on the mining materials. Obtaining the spectroscopic data may involve measuring the spectroscopic data at one or more of the stages of the hydrocarbon extraction and recovery process. The spectroscopic data may be obtained at the same time as the reference standard, after the reference standard is obtained, and/or before the reference standard is obtained. For example, the reference standard may be obtained at the same location, with the same equipment, and/or within a specific time period (e.g., obtaining the calibration reference standard and spectroscopic data within one minute of each other, within fifteen minutes of each other, within one hour of each other, within a twenty-four hour period of each other, or within a week of each other).

At block 306, measured spectroscopic data from the one or more hydrocarbon extraction and recovery stages are compared with the reference standard to form refined spectroscopic data. For example, the measured spectroscopic data may be compared with the reference standard by using the reference standard as a filter to remove background noise from the measured spectroscopic data. This comparing may include forming a ratio between the measured spectroscopic data and the reference standard or subtracting the reference standard from the measured spectroscopic data.

At block 308, one or more mining properties may be determined from the refined spectroscopic data. The determination may include comparing the refined spectroscopic data with previously obtained models, charts, graphs, or other information to determine the respective properties. The spectral data (e.g., peak position, intensity, shape, breadth, etc.) in the refined spectroscopic data may include all parts and/or discrete parts of the received spectrum and may be calibrated to lab measurements, which may be from ore and/or ground-truthing data, and may be used as a training set. Lab measurements may include XRD responses, SGR responses, XRF responses, Dean Stark bitumen percentages, grain sizes, TEOM responses, TOC responses, GC responses, bitumen molecular weight responses (e.g., SIMDIST measurements), SARA measurements, and/or bitumen viscosity responses. Chemometric models may be used to understand and to estimate mining properties from the spectroscopic data of unknown samples in the mine or mining materials. Values for unknowns of spectroscopic data may be estimated from known relationships between spectral responses (e.g., due to physical and chemical properties of the mining material) and ground-truthing data in the training data.

At block 310, the one or more mining properties may be utilized to adjust one or more of the operations of the hydrocarbon extraction process. The one or more properties may be utilized by providing the properties to the operators in the control room via a display or other notification mechanism. The adjustments to the hydrocarbon extraction process may include performing the adjustments noted in block 114 of FIG. 1.

Beneficially, the use of a standard reference may be utilized in manner to lessen uncertainty in the data. Further, if the standard reference is obtained within a specific time window of the acquiring of the spectroscopic data, the noise and other artifacts may be lessened by using the same spectrometer to obtain the reference standard and the measured spectroscopic data.

Moreover, in certain embodiments, the adjustments to the measured spectroscopic data may include weighting the spectroscopic data from one or more portions of a spectrum or from different spectra with different weights based on the environmental conditions. The environmental conditions may include the amount of light level (e.g., amount of sunshine), amount of rain, amount of snow, amount of fog, amount of ice, temperature range, and the like. The spectral data (e.g., peak position, intensity, shape, breadth, etc.) from all parts or discrete parts of the received spectrum may be weighted to compensate for environmental conditions as compared to calibrations from lab measurements of ore (e.g., ground-truthing data or training set). Lab measurements may include XRD responses, SGR responses, XRF responses, Dean Stark bitumen percentages, grain sizes, TEOM responses, TOC responses, GC responses, bitumen molecular weight responses (e.g., SIMDIST measurements), SARA measurements, and/or bitumen viscosity responses.

Figure 4:
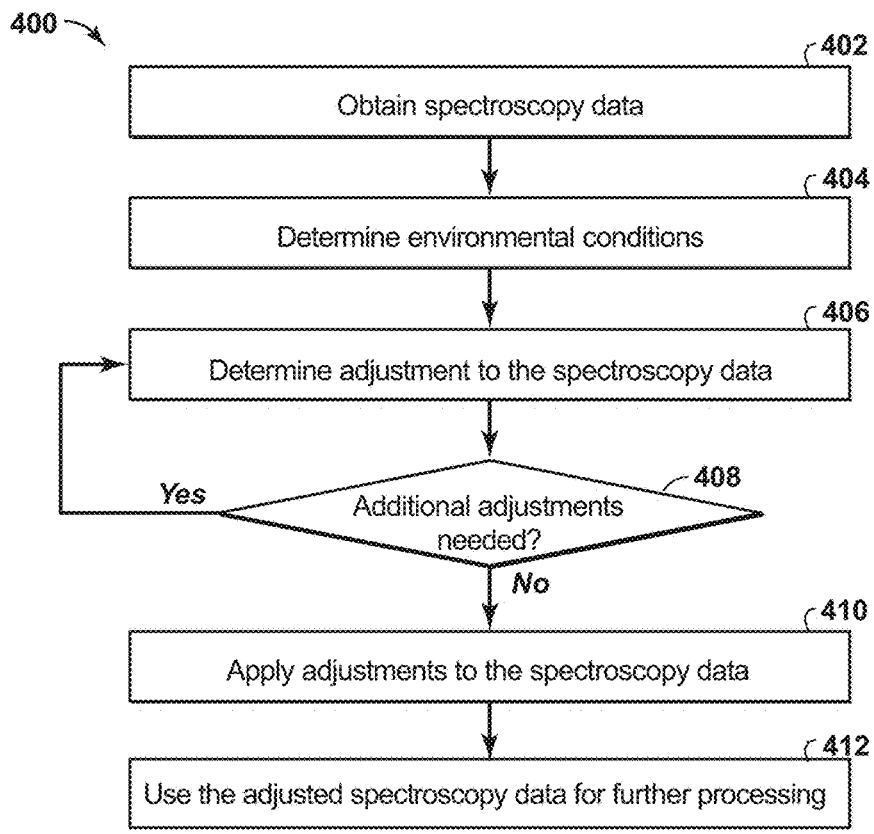
FIG. 4 is a flow diagram of an exemplary method of calibrating measured spectroscopic data in a hydrocarbon extraction process.

As an example, FIG. 4 is a flow diagram 400 of an exemplary method of weighting the spectroscopic data in a hydrocarbon extraction process in accordance with an exemplary embodiment of the present techniques. In this method, the spectroscopic data are weighted in one or more of the hydrocarbon extraction stages in a hydrocarbon extraction process. The weighting of the spectroscopic data may be utilized to compensate for environmental variables or conditions in the various stages.

In this diagram 400, spectroscopic data are obtained, as shown in block 402. The spectroscopic data may be obtained from one or more of the stages, such as block 106 or 110 of FIG. 1. At block 404, environmental conditions may be determined. The determination of the environmental conditions may include using sensors to determine environmental conditions. For example, the environmental conditions may include the amount of sunshine, amount of rain, amount of snow, amount of fog, amount of ice, temperature range, and the like.

At block 406, an adjustment to the spectroscopic data are determined. The adjustment may include different mathematical adjustments to the spectroscopic data. For example, the adjustments may include changing the weights to be applied to the spectroscopic data at the different hydrocarbon extraction stages. The weights may be applied to specific portions of the spectroscopic data, which may include different spectral features (e.g., peak position, intensity, shape, breadth, etc.) from all parts or discrete parts of the received spectrum. The weighting of the spectroscopic data may be based on the environmental conditions in the respective stages and/or may be adjusted individually at the different stages.

At block 408, a determination is made if additional adjustments are needed. The determination may include determining different weights for different portions of the spectrum or for different properties represented in the spectroscopic data. If additional adjustments are needed, the process may perform block 406 again for the additional adjustment.

If no additional adjustments are needed, then the adjustments are applied to the spectroscopic data, as shown in block 410. The adjustments may include weighting the spectroscopic data to form the adjusted spectroscopic data. For example, fog interferes with the visible wavelengths, as a result the spectroscopic data for the visible wavelengths may be multiplied by an adjustment factor, for example by 0.5, to lessen the impact of fog on the analysis.

At block 412, the adjusted spectroscopic data may be used for further processing. For example, the further processing may include obtaining a reference standard (e.g., block 302 of FIG. 3); obtaining spectroscopic data (e.g., block 304 of FIG. 3); comparing spectroscopic data with the reference standard to form the refined spectroscopic data (e.g., block 306 of FIG. 3) and/or determining the one or more mining properties from the refined spectroscopic data (e.g., block 308 of FIG. 3).

Figure 5A:
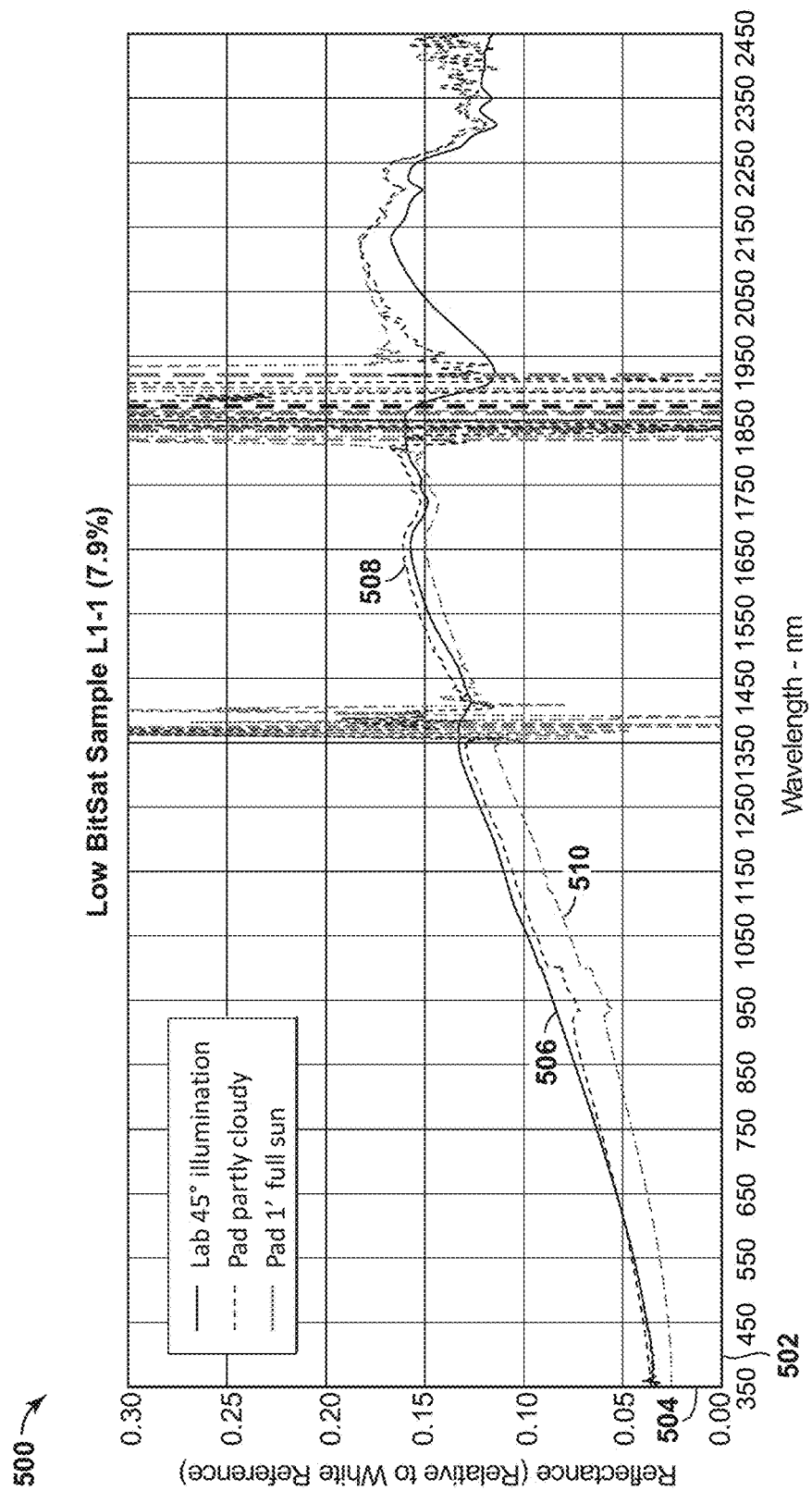
FIGS. 5A and 5B are exemplary charts illustrating reflectance compared with wavelength and are associated with calibrations for varying atmospheric conditions.

As an example, FIG. 5A is an exemplary chart 500 showing reflectance compared with wavelength in accordance with an exemplary embodiment of the present techniques. In this chart 500, the reflectance responses 506, 508, and 510 are shown along the reflectance axis 504 (e.g., relative to a white reference, as the standard reference, which increases in value in a direction upward from the wavelength axis 502) and the wavelength axis 502 in nanometers (nm). The reflectance response 506 represents laboratory measurements obtained under artificial light at an illumination angle of 45°, the reflectance response 508 represents measured spectroscopic data obtained under natural illumination during a period of time that was partly cloudy, and the reflectance response 510 represents measured spectroscopic data obtained under natural illumination during a period of time that exhibited full sunshine. These reflectance responses 506, 508, and 510 are shown for wavelengths from 350 nm to 2450 nm (e.g., from a portion of the ultraviolet spectral range to visible spectral range to a portion of the infrared spectral range). By comparing the responses obtained under natural illumination 508 and 510 to the response obtained under artificial illumination 506, the zones of interference due to the environmental conditions become apparent. Thus, as seen in chart 500, the portions of responses 508 and 510 at wavelengths from 1350 nm to 1450 nm and from 1800 nm to 1950 nm varied widely and exhibited reflectance values of from 0.0 to 0.30. Similarly, the portion of responses 508 and 510 at wavelengths from 900 to 1025 nm exhibited distortions to a lesser degree. Thus, the atmospheric/environmental interferences (i.e., those from the sunlight and clouds) distorted the spectroscopic data at certain wavelengths. Accordingly, it may be desirable to discard or weight the measured spectroscopic data obtained at those wavelengths to a lower level to lessen the distortion.

Figure 5B:
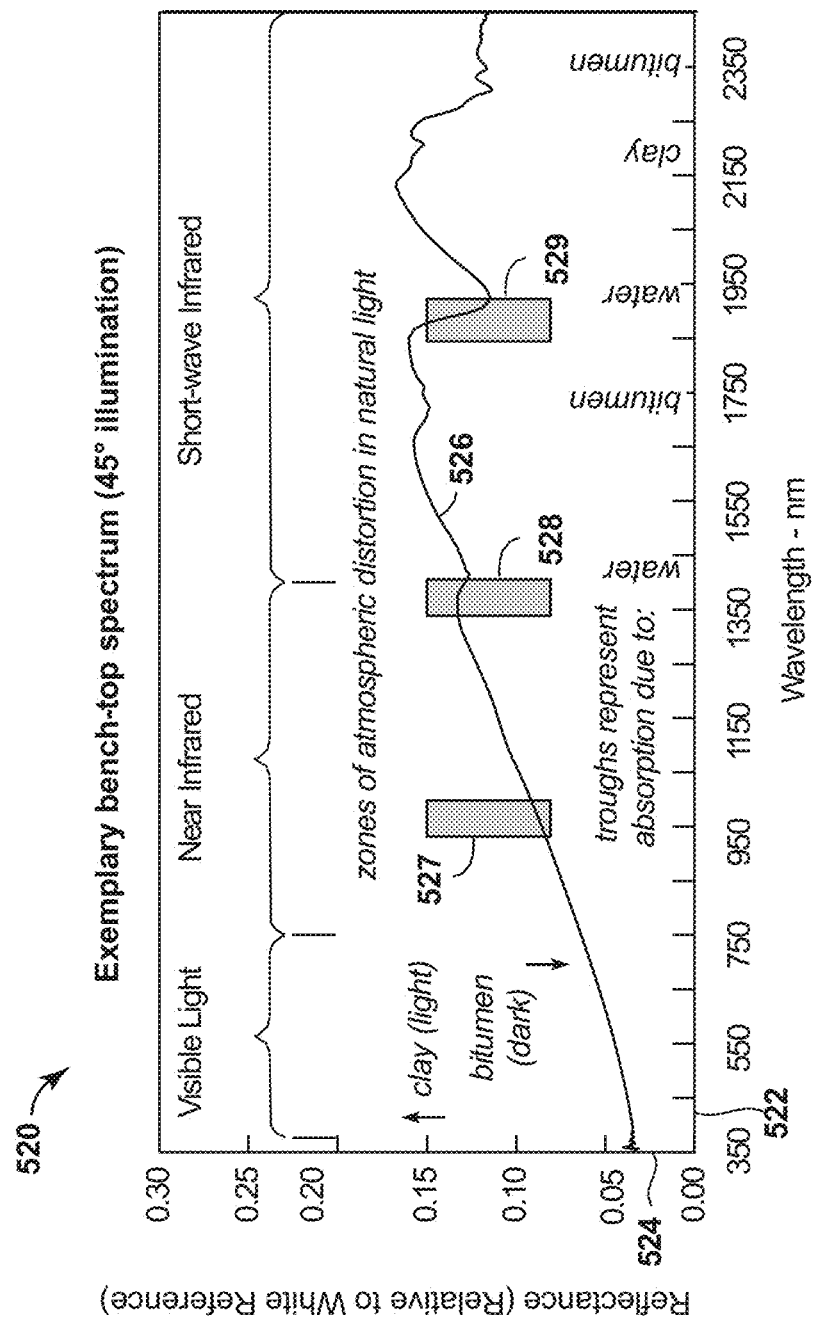

FIG. 5B is another exemplary chart 520 illustrating reflectance (e.g., relative to a white reference) compared with wavelength in accordance with an exemplary embodiment of the present techniques. The chart 520 is an exemplary bench-top spectrum example at a 45° angle of illumination, which includes wavelengths from visible light to near infrared to short-wave infrared. In this chart 520, the reflectance response 526 is shown along the reflectance axis 524, which increase in value in a direction upward from the wavelength axis 522, and the wavelength axis 522 in nm. The troughs along the reflectance response 526 are representative of the adsorption due to various material. Thus, as seen in chart 520, the reflectance response 526 is higher for clay (e.g., lighter) and lower for bitumen (e.g., darker). For example, the trough around 1400 nm to 1450 nm is associated with the adsorption by water, the trough around 1700 nm to 1750 nm is associated with bitumen, the trough around 1900 nm to 1950 nm is associated with the adsorption by water, the trough around 2150 nm to 2250 nm is associated with the adsorption by clay, and the trough around 2300 nm to 2400 nm is associated with the adsorption by bitumen. Accordingly, the entire spectrum provides additional information for the mining properties. While, FIG. 5B illustrates troughs related to the different absorptions of the materials, chart 520 does not illustrate the atmospheric distortions that were seen in FIG. 5A at the wavelengths associated with zone 527, 528, and 529. Therefore, FIG. 5B could be used as a reference standard to create a filter to adjust and calibrate reflectances obtained different conditions of natural illumination (e.g., full sunshine, clouds, etc.).

Figure 6A:
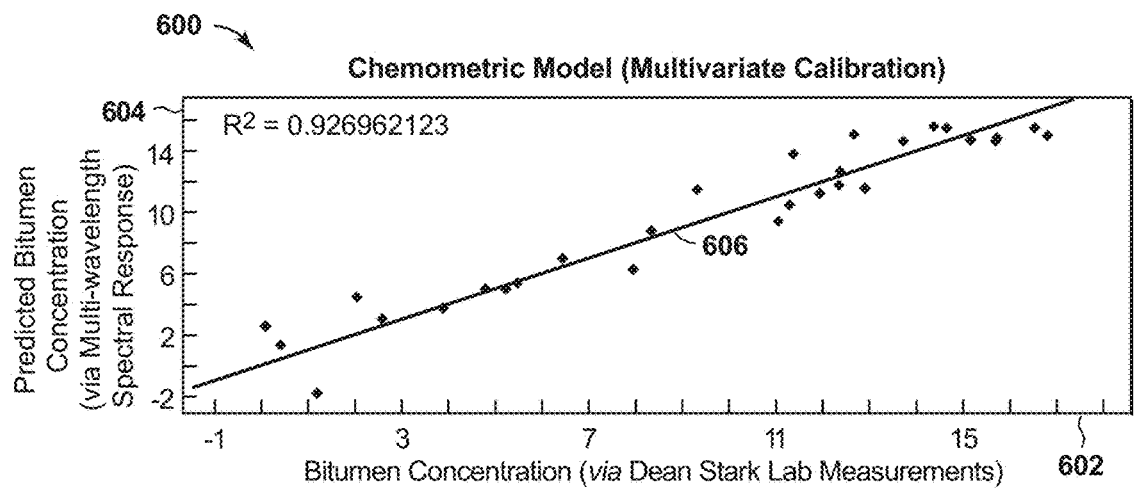
FIGS. 6A and 6B are exemplary charts illustrating exemplary methods of the present techniques.

FIG. 6A is an exemplary chart 600 associating the bitumen concentration predicted via multi-wavelength spectral responses compared with bitumen concentration measured using laboratory methods. In chart 600, the bitumen concentration predicted with multi-wavelength spectral analysis (such as using the spectroscopy methods described herein) is shown on axis 604 and the bitumen concentration for the same sample measured by laboratory methods (e.g., Dean Stark Lab Measurements) is shown on axis 602. Through chemometric modeling (e.g., a multivariate calibration) the predicted bitumen concentration and the measured concentration can be fit together, and as seen in chart 600 the data fit 606 from the reflectance response has a coefficient of determination ($R^2$) of 0.92696213

Figure 6B:
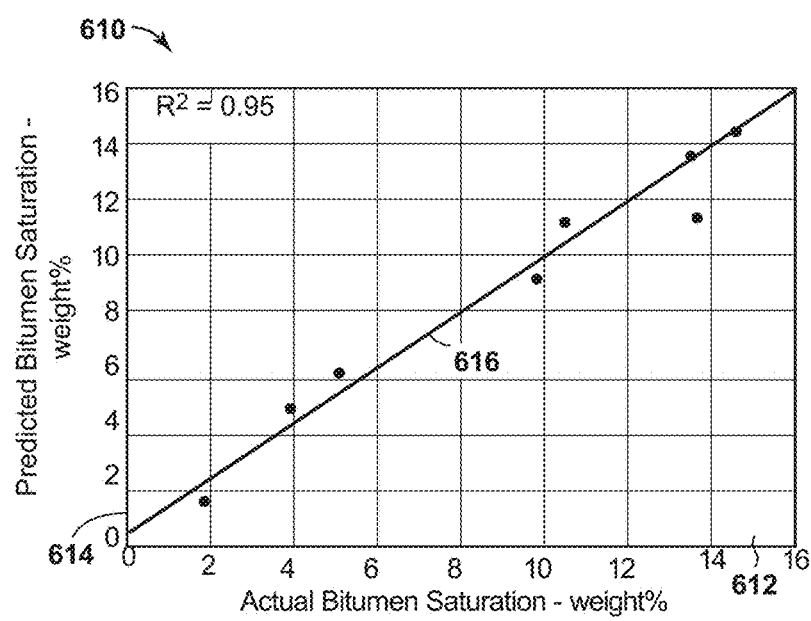

FIG. 6B is an exemplary chart 610 associating the predicted bitumen saturation compared with actual bitumen saturation in accordance with an exemplary embodiment of the present techniques. In this chart 610, the correlation bitumen saturation response 616 is shown along the predicted bitumen saturation axis 614 in weight percentage (weight %) and the actual bitumen saturation axis 612 in weight %. The correlation bitumen saturation response 616 has a coefficient of determination ($R^2$) of 0.95. Thus, as shown in FIGS. 6A and 6B the spectroscopic data can be calibrated and ground-truthed with physical laboratory measurements. Furthermore, as seen in FIGS. 6A and 6B the spectroscopic data can be used to accurately predict the bitumen concentration and bitumen saturation in samples without expensive and time consuming physical laboratory measurements.

Figure 7A:
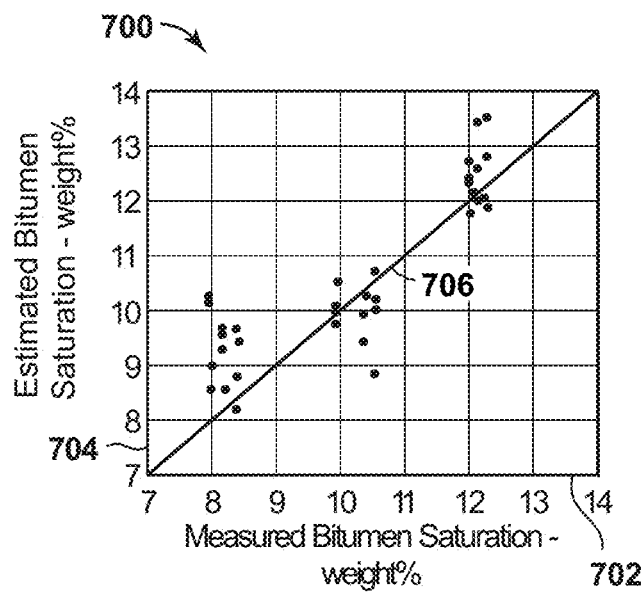
FIGS. 7A to 7F are exemplary charts associated with measurements taken at different wavelengths.

FIGS. 7A to 7F illustrate analyses using different portions of the wavelength spectra. FIG. 7A is an exemplary chart 700 associated with estimated bitumen saturation compared with actual bitumen saturation for the visible light spectrum (i.e., 350 nm to 750 nm). In chart 700, the correlation bitumen saturation response 706 is shown along the estimated bitumen saturation axis 704 in weight % and the actual bitumen saturation axis 702 in weight %. As seen in chart 700, the comparison of the bitumen saturations for only the visible light spectrum has an average error of about ±0.9 weight % and a maximum error in the range between +2.3 weight % and −1.7 weight %.

Figure 7B:
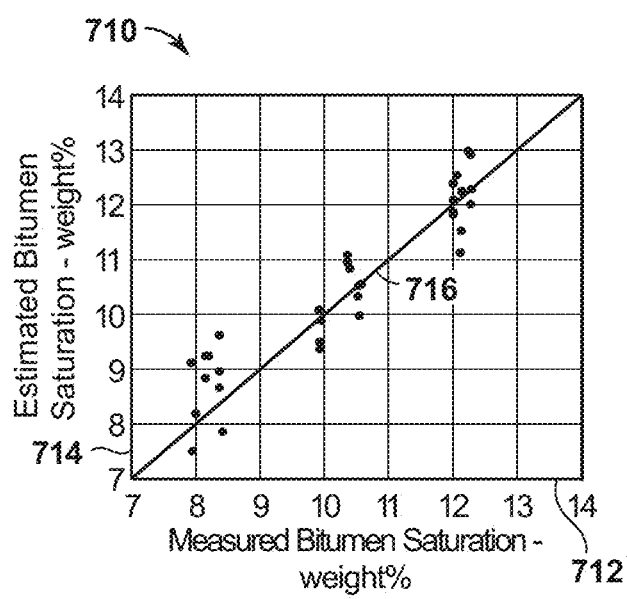
Figure 7C:
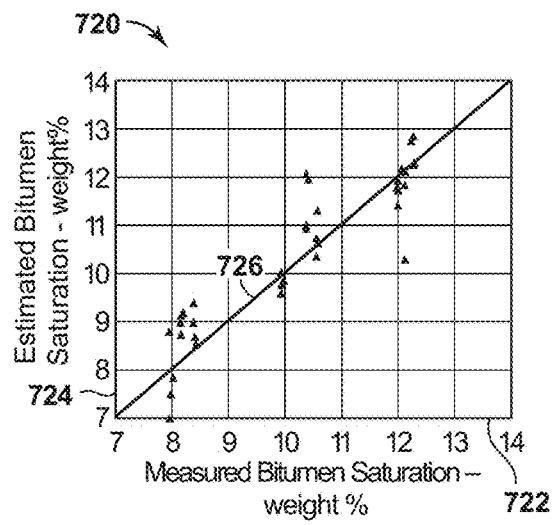

FIG. 7B is an exemplary chart 710 associated with estimated bitumen saturation compared with actual bitumen saturation for a spectrum of 2150 nm to 2250 nm. In chart 710, the correlation bitumen saturation response 716 is shown along the estimated bitumen saturation axis 714 in weight % and the actual bitumen saturation axis 712 in weight %. As seen in chart 710, the comparison of the bitumen saturations for only the discrete wavelengths of 2150 nm to 2250 nm has an average error of about ±0.7 weight % and a maximum error in the range between +1.3 weight % and −1.7 weight %. FIG. 7C is an exemplary chart 720 associated with estimated bitumen saturation compared with actual bitumen saturation at wavelengths of from 1700 nm to 1750 nm. In chart 720, the correlation bitumen saturation response 726 is shown along the estimated bitumen saturation axis 724 in weight % and the actual bitumen saturation axis 722 in weight %. As seen in chart 720 the comparison of the bitumen saturations for discrete wavelengths of 1700 nm to 1750 nm has an average error of about ±0.7 weight % and a maximum error in the range between +1.7 weight % and −1.8 weight %.

Figure 7D:
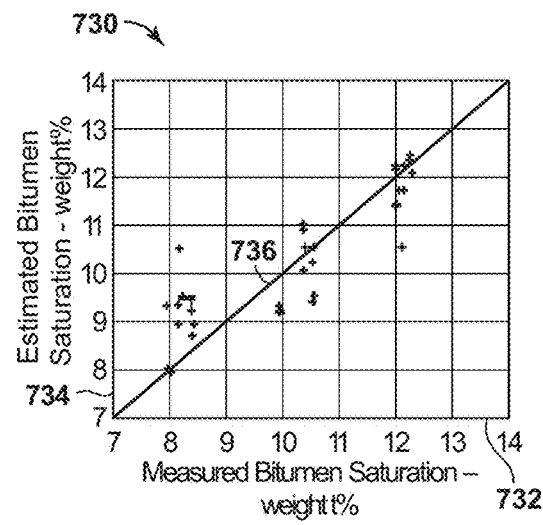

FIG. 7D is an exemplary chart 730 associated with estimated bitumen saturation compared with actual bitumen saturation for at wavelengths of 2300 nm to 2400 nm. In chart 730, the correlation bitumen saturation response 736 is shown along the estimated bitumen saturation axis 734 in weight % and the actual bitumen saturation axis 732 in weight %. The chart 730 includes a comparison of the bitumen saturations for discrete wavelengths of 2300 nm to 2400 nm and has an average error of about ±0.7 weight % and a maximum error in the range between of +2.4 weight % and −1.6 weight %.

Figure 7E:
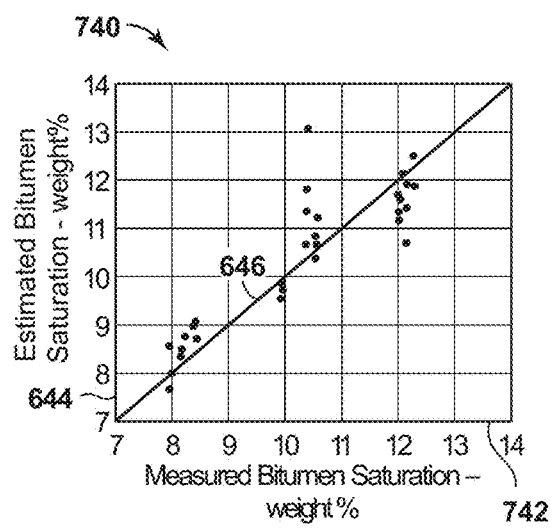

FIG. 7E is an exemplary chart 740 associated with estimated bitumen saturation compared with actual bitumen saturation for wavelengths of from 750 nm to 2450 nm. In chart 740, the correlation bitumen saturation response 746 is shown along the estimated bitumen saturation axis 744 in weight % and the actual bitumen saturation axis 742 in weight %. The chart 740 includes a comparison of the bitumen saturations for only for non-visible (e.g., for discrete wavelengths from 750 nm to 2450 nm) and has an average error of about ±0.7 weight % and a maximum error in the range between of +2.7 weight % and −1.4 weight %.

Figure 7F:
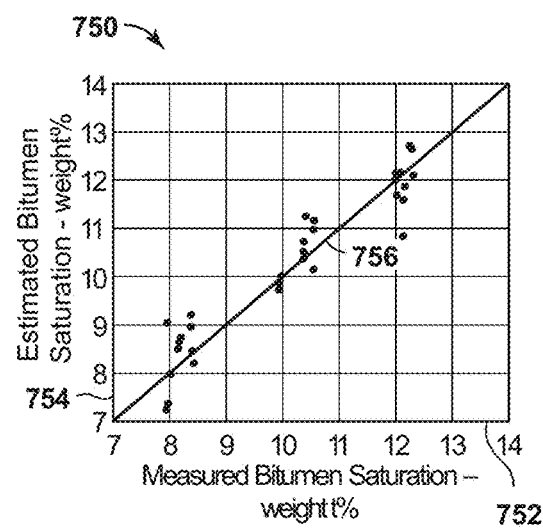

FIG. 7F is an exemplary chart 750 associated with estimated bitumen saturation compared with actual bitumen saturation for all of the measured wavelengths. In chart 750, the correlation bitumen saturation response 756 is shown along the estimated bitumen saturation axis 754 in weight % and the actual bitumen saturation axis 7552 in weight %. The chart 750 includes a comparison of the bitumen saturations for all measured wavelengths (i.e., for wavelengths of 350 nm to 2450 nm) and has an average error of about ±0.5 weight % and a maximum error in the range between of +1.1 weight % and −1.3 weight %. Beneficially, by using the all of the measured wavelengths, the average errors and the range of maximum errors are reduced. That is, when comparing the average error and range of errors in FIGS. 7A to 7D that only looked at discrete portions of the wavelength spectra, and with FIG. 7E that only looked at the non-visible spectra, when looking at the entire spectrum in FIG. 7F (e.g., from 350 nm to 2500 nm) the error associated with the estimated value can be reduced. Therefore, it may be advantageous to measure the spectroscopic data across the entire wavelength spectrum, or from 350 nm to 2500 nm, as compared to measuring only discrete portions of the wavelength spectrum.

Figure 8A:
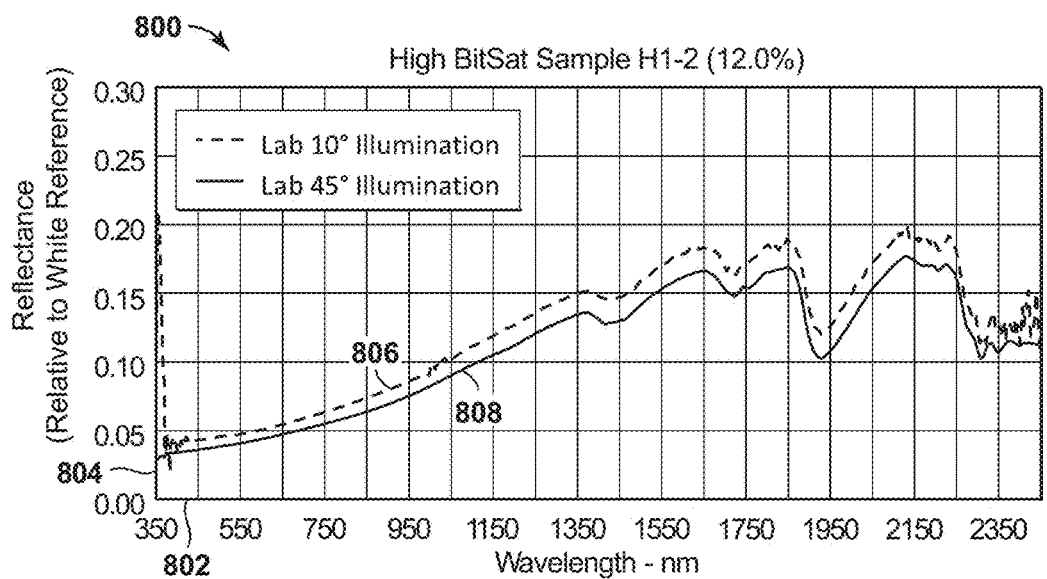
FIGS. 8A and 8B are exemplary charts associated with measurements taken at different illumination angles.
Figure 8B:
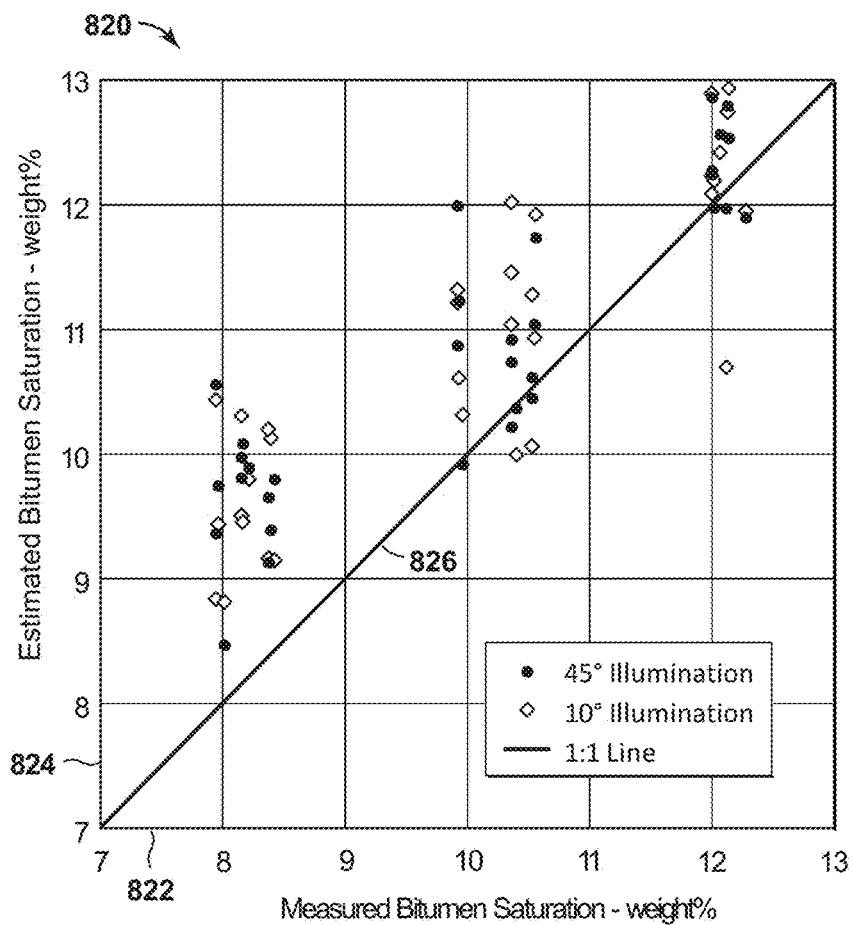

FIGS. 8A and 8B are exemplary charts 800 and 820 that illustrate measurements taken at different illumination angles that can be associated with the height/position of the sun relative to the sample at different times of the day and different times of the year. In particular, FIG. 8A is an exemplary chart 800 associated with reflectance (e.g., relative to a white reference) compared with wavelength. The chart 800 is an exemplary bench-top spectrum example at an angle of 45° for illumination (e.g., summer illumination) and at an angle of 10° for illumination (e.g., winter illumination). The measured wavelengths are from visible light to near infrared to short-wave infrared. In this chart 800, the reflectance responses 806 and 808 are shown along the reflectance axis 804, which increase in value in a direction upward from the wavelength axis 802, and the wavelength axis 802 in nm. The reflectance response 806 represents the reflectance with an illumination angle of 10°, while the reflectance response 808 represents the reflectance with an illumination angle of 45°. Both of these responses 806 and 808 have troughs due to zones of atmospheric distortion in the natural light. As shown by the chart 800, the responses 806 and 808 are closely related over the entire spectrum of from 350 nm to 2450 nm.

FIG. 8B is an exemplary chart 820 associated with estimated bitumen saturation compared with actual bitumen saturation for different illumination angles. In this chart 820, the correlation bitumen saturation response 826 is shown along the estimated bitumen saturation axis 824 in weight % and the actual bitumen saturation axis 822 in weight %. The chart 820 includes a comparison of the bitumen saturations for different illumination angles. The points of solid black represent data associated with an angle of 45° for illumination, while points with white center represent data associated with an angle of 10° for illumination. The points at an angle of 45° for illumination have an average error of about ±1.1 weight % and a maximum error in the range between of +2.6 weight % and −0.4 weight %, while the points at an angle of 10° for illumination have an average error of about ±1.2 weight % and a maximum error in the range between of +2.5 weight % and −1.4 weight %. Beneficially, by using the all of the measured wavelengths (e.g., wavelengths from 350 nanometers to 2450 nanometers), the average errors and the range of maximum errors are similar regardless of the angle of illumination.

Figure 9A:
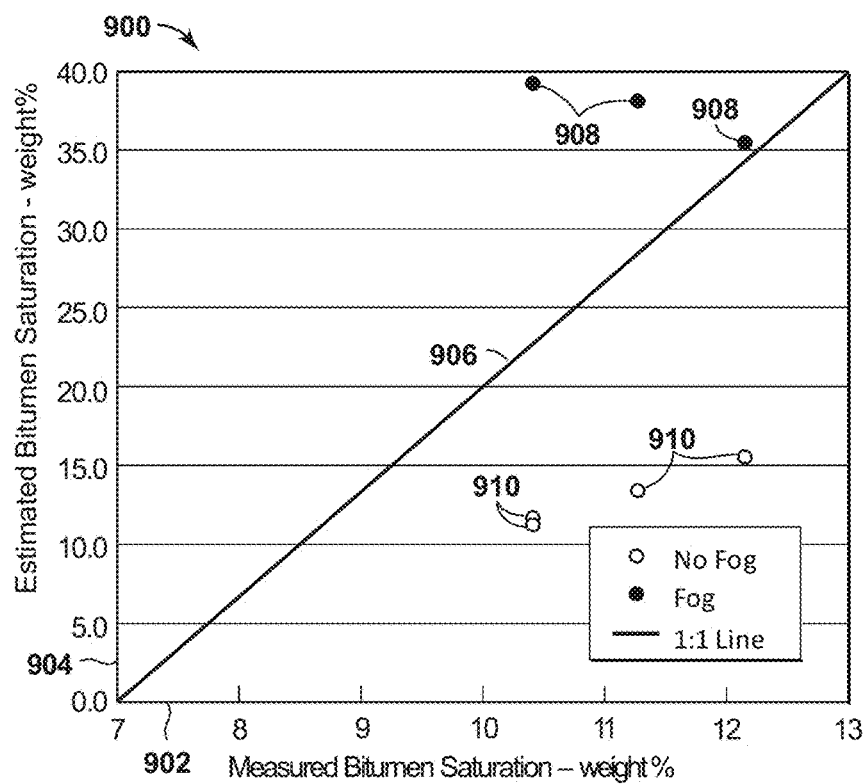
FIGS. 9A and 9B are exemplary charts associated with measurements taken at different environmental conditions.
Figure 9B:
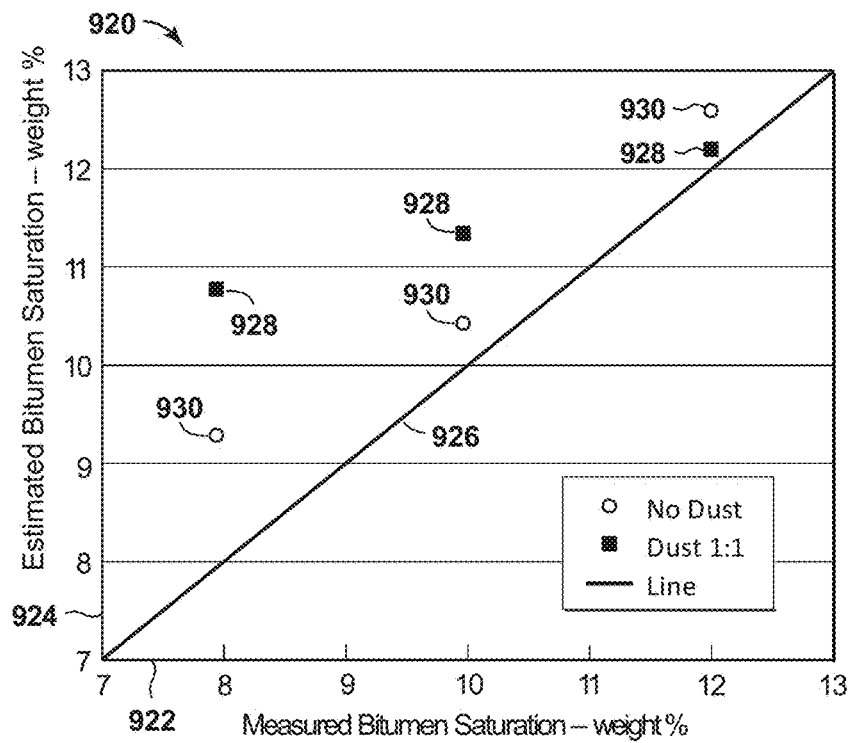

FIGS. 9A and 9B are exemplary charts 900 and 920 associated with environmental conditions in accordance with an exemplary embodiment of the present techniques. In particular, FIG. 9A is a chart 900 of the environmental conditions involving fog or no fog, while 9B is a chart 920 of the environmental conditions involving dust or no dust.

FIG. 9A is an exemplary chart 900 associated with estimated bitumen saturation compared with actual bitumen saturation for fog related conditions. In this chart 900, the correlation bitumen saturation response 906 is shown along the estimated bitumen saturation axis 904 in weight % and the actual bitumen saturation axis 902 in weight %. The chart 900 includes a comparison of the bitumen saturations for different environmental conditions involving fog. The points of solid black, such as points 908, represent data associated with fog conditions, while points with a white center, such as points 910 represent data associated with no fog conditions. As such, the fog distorts the spectroscopic data, but may be filtered to adjust to remove the distortion.

FIG. 9B is an exemplary chart 920 associated with estimated bitumen saturation compared with actual bitumen saturation for dust related conditions. In this chart 920, the correlation bitumen saturation response 926 is shown along the estimated bitumen saturation axis 924 in weight % and the actual bitumen saturation axis 922 in weight %. The chart 920 includes a comparison of the bitumen saturations for different environmental conditions involving dust. The points of solid black, such as points 928, represent data associated with dust conditions, while points with a white center, such as points 930, represent data associated with no dust conditions. As such, the dust distorts the spectroscopic data, but may be filtered to remove the distortion.

Figure 10:
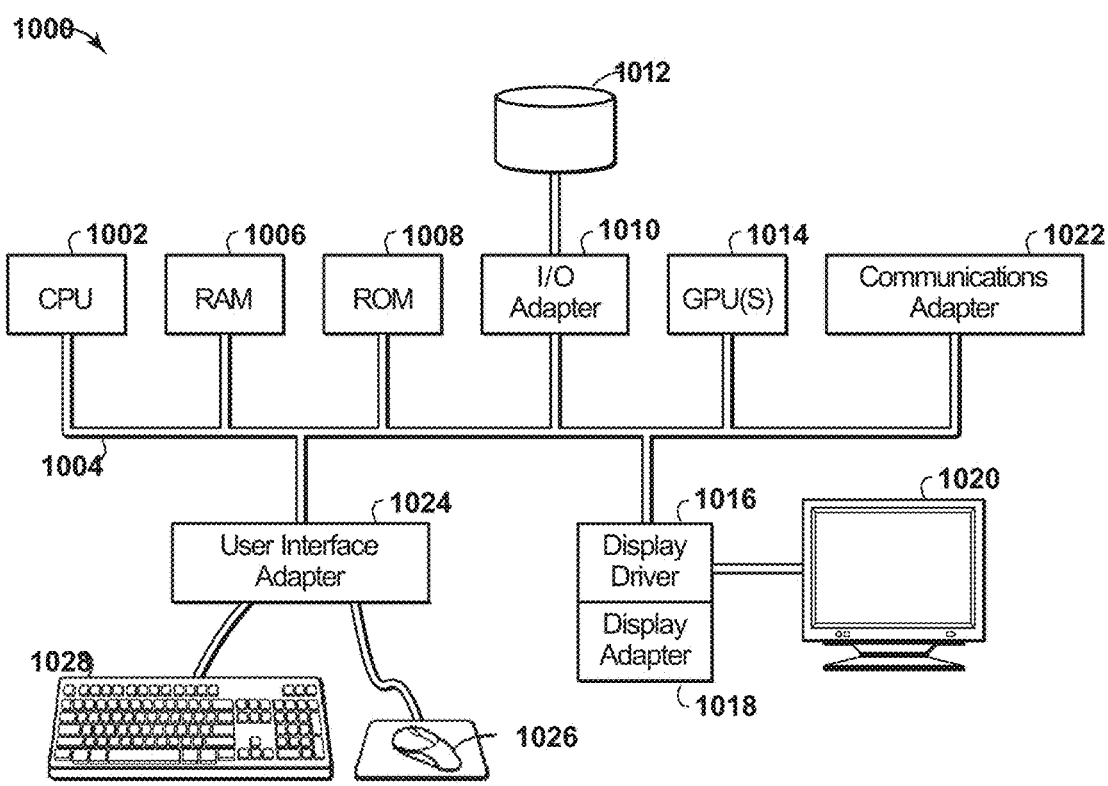
FIG. 10 is a block a diagram of a computer system that may be used with embodiments of the present techniques.

FIG. 10 is a block diagram of a computer system 1000 in accordance with an exemplary embodiment of the present techniques. A central processing unit (CPU) 1002 is coupled to system bus 1004. The CPU 1002 may be any general-purpose CPU, although other types of architectures of CPU 1002 (or other components of exemplary system 1000) may be used as long as CPU 1002 (and other components of system 1000) supports the inventive operations as described herein. The CPU 1002 may execute the various logical instructions according to various exemplary embodiments. For example, the CPU 1002 may execute machine-level instructions for performing processing according to the operational flow described above.

The computer system 1000 may also include computer components such as a random access memory (RAM) 1006, which may be SRAM, DRAM, SDRAM, or the like. The computer system 1000 may also include read-only memory (ROM) 1008, which may be PROM, EPROM, EEPROM, or the like. RAM 1006 and ROM 1008 hold user and system data and programs, as is known in the art. The computer system 1000 may also include an input/output (I/O) adapter 1010, one or more graphical processing units 1014, a communications adapter 1022, a user interface adapter 1024, and a display adapter 1018. The I/O adapter 1010, the user interface adapter 1024, and/or communications adapter 1022 may, in certain embodiments, enable a user to interact with computer system 1000 in order to input information.

The I/O adapter 1010 preferably connects a storage device(s) 1012, such as one or more of hard drive, compact disc (CD) drive, floppy disk drive, tape drive, etc. to computer system 1000. The storage device(s) may be used when RAM 1006 is insufficient for the memory requirements associated with storing data for operations of embodiments of the present techniques. The data storage of the computer system 1000 may be used for storing information and/or other data used or generated as disclosed herein. The communications adapter 1022 may couple the computer system 1000 to a network (not shown), which may enable information to be input to and/or output from system 1000 via the network (for example, the Internet or other wide-area network, a local-area network, a public or private switched telephony network, a wireless network, any combination of the foregoing). User interface adapter 1024 couples user input devices, such as a keyboard 1028, a pointing device 1026, and the like, to computer system 1000. The display adapter 1018 is driven by the CPU 1002 to control, through a display driver 1016, the display on a display device 1020. Information and/or representations pertaining to a portion of a hydrocarbon extraction process or a hydrocarbon extraction simulation, such as displaying data corresponding to a physical or financial property of interest, may thereby be displayed, according to certain exemplary embodiments.

The architecture of system 1000 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

For example, the system 1000 may be a computer system utilized in a hydrocarbon extraction process, as the control unit and/or the spectrometers, for example. The system may include a processor; memory in communication with the processor; and a set of instructions stored in memory and accessible by the processor. The system may be configured to display the hydrocarbon extraction process or spectroscopic data from one or more of the stages of the hydrocarbon extraction process. The set of instructions, when executed by the processor for a spectrometer or control unit, may be configured to: measure spectroscopic data concurrently with the performance of one of the stages in the process; communicate spectroscopic data between spectrometers or a control unit. Further, set of instructions, when executed by the processor for a spectrometer or control unit, may be configured to: communicate with one of the mine face spectrometer, one or more stage spectrometers, and any combination thereof and to provide one or more notifications for an adjustment to the plurality of operations based on the one of the mine face spectrometer, one or more stage spectrometers, and any combination thereof (e.g., measure stage spectroscopic data in the surge bin, measure stage spectroscopic data as the mining material is transported by the conveyor, measure stage spectroscopic data as the mining material is mixed with the liquid, measure stage spectroscopic data as the froth stream is conducted away from the primary separation cell unit and/or measure stage spectroscopic data as the middling stream is conducted away from the primary separation cell unit).

Further, the set of instructions may be utilized to integrate other data and information with the spectroscopic data. For example, the set of instructions may also be configured to integrate mining data for the mining region with the one of the mine face spectroscopic data, the stage spectroscopic data, and any combination thereof; to generate a stratigraphic framework with the mining data and to compute stacking patterns within the stratigraphic framework based on the one of the mine face spectroscopic data, the stage spectroscopic data, and any combination thereof; to: obtain a reference standard associated with one of the mine face spectroscopic data and the stage spectroscopic data; compare the reference standard with the one of the mine face spectroscopic data and the stage spectroscopic data to form refined spectroscopic data; determine one or more mining properties from the refined spectroscopic data, wherein the one or more mining properties comprise one or more of mineralogy, bitumen saturation, bitumen viscosity, and grain size distribution; and determine the one or more notifications based on the one or more mining properties; and/or to integrate the one or more mining properties with a model of the mining region or hydrocarbon extraction stages. Further still, the set of instructions may be configured to: determine an environmental condition associated with the one of the mine face spectroscopic data, the stage spectroscopic data, and any combination thereof; determine one or more adjustments to the one of the mine face spectroscopic data, the stage spectroscopic data, and any combination thereof based on the determined environmental condition; and apply the one or more adjustments to the one of the mine face spectroscopic data, the stage spectroscopic data, and any combination thereof prior to providing the one or more notifications; and/or to apply different weights to different portions of the one of the mine face spectroscopic data, the stage spectroscopic data, and any combination thereof based on the environmental conditions.

In view of the many possible embodiments to which the principles of the disclosed invention may be applied, it should be recognized that the illustrative embodiments are only preferred examples of the invention and should not be taken as limiting the scope of the invention.

What is claimed is:

1. A method of performing a hydrocarbon extraction process having a plurality of hydrocarbon extraction stages comprising:
   a) removing mining materials from a mining region as one of the plurality of hydrocarbon extraction stages;
   b) obtaining mine face spectroscopic data concurrently with removal of mining materials from a mine face associated with the mining region;
   c) performing one or more operations on the mining material removed from the mining region in a subsequent one of the plurality of hydrocarbon extraction stages;
   d) obtaining one or more stage spectroscopic data concurrently with the performing of the one or more operations on the mining material;
   e) adjusting the one or more operations based on one of the mine face spectroscopic data, the stage spectroscopic data, and any combination thereof; and
   f) separating hydrocarbons from the mining materials after adjusting the one or more operations;
   wherein the method further comprises:
      integrating the one of the mine face spectroscopic data, the stage spectroscopic data, and any combination thereof with mining data for the mining region; and
      generating a stratigraphic framework with the mining data and computing stacking patterns within the stratigraphic framework based on the one of the mine face spectroscopic data, the stage spectroscopic data, and any combination thereof.

2. The method of claim 1, wherein separating the hydrocarbons from the mining materials comprises performing a separation process in a primary separation cell unit to form a froth stream, a middling stream, and a coarse tailings stream.

3. The method of claim 1, wherein the mining data comprise one or more of heavy oil hand sample analysis data, well log data, core analysis data, ground penetrating radar data, and seismic data.

4. The method of claim 1, wherein adjusting the one or more operations based on one of the mine face spectroscopic data, the stage spectroscopic data and any combination thereof further comprises:
   obtaining a reference standard associated with one of the mine face spectroscopic data and the stage spectroscopic data;
   comparing the reference standard with the one of the mine face spectroscopic data and the stage spectroscopic data to form refined spectroscopic data;
   determining one or more mining properties from the refined spectroscopic data; and
   using the one or more mining properties to adjust the one or more operations.

5. The method of claim 4, wherein the one or more mining properties comprise one or more of mineralogy, bitumen saturation, bitumen viscosity, and grain size distribution.

6. The method of claim 1, further comprising integrating the one or more mining properties with a model of the mining region or hydrocarbon extraction stages.

7. The method of claim 1, wherein adjusting the one or more operations based on the mine face spectroscopic data and/or the stage spectroscopic data comprises:
   determining environmental conditions associated with the one of the mine face spectroscopic data, the stage spectroscopic data, and any combination thereof;
   determining one or more adjustments to the one of the mine face spectroscopic data, the stage spectroscopic data, and any combination thereof based on the determined environmental conditions; and
   applying the one or more adjustments to the one of the mine face spectroscopic data, the stage spectroscopic data, and any combination thereof before adjusting the one or more operations based on the one of the mine face spectroscopic data, the stage spectroscopic data, and any combination thereof.

8. The method of claim 7, wherein the one or more adjustments comprise applying different weights to different portions of the one of the mine face spectroscopic data, the stage spectroscopic data, and any combination thereof based on the environmental conditions.

9. The method of claim 1, wherein the one of the mine face spectroscopic data, the stage spectroscopic data, and any combination thereof comprise two or more of at least a portion of the ultraviolet spectral range, at least a portion of the visible spectral range, at least a portion of the infrared spectral range, at least a portion of near-infrared spectral range, and at least a portion of the short-wavelength infrared spectral range.

10. The method of claim 1, wherein the one of the mine face spectroscopic data, the stage spectroscopic data, and any combination thereof comprises measured reflectance data for wavelengths in the range between 350 nanometers and 2500 nanometers.

11. The method of claim 1, wherein obtaining one or more stage spectroscopic data concurrently with the performing of the one or more operations on the mining material comprises passively measuring reflectance data from the mining material.

12. The method of claim 1, wherein obtaining one or more stage spectroscopic data concurrently with the performing of the one or more operations on the mining material further comprises measuring spectroscopic data as the mining material is transported from the mining face.

13. The method of claim 1, wherein obtaining one or more stage spectroscopic data concurrently with the performing of the one or more operations on the mining material further comprises measuring spectroscopic data as the mining material is disposed in a surge bin.

14. The method of claim 1, wherein obtaining one or more stage spectroscopic data concurrently with the performing of the one or more operations on the mining material further comprises measuring spectroscopic data as the mining material is transported on a conveyor.

15. The method of claim 1, wherein obtaining one or more stage spectroscopic data concurrently with the performing of the one or more operations on the mining material further comprises measuring spectroscopic data as the mining material is mixed with a liquid in a mixing unit.

16. The method of claim 1, wherein obtaining one or more stage spectroscopic data concurrently with the performing of the one or more operations on the mining material further comprises measuring spectroscopic data as the mining material is separated in a primary separation cell unit to form a froth stream, a middling stream and a coarse tailings stream.

17. The method of claim 1, wherein obtaining one or more stage spectroscopic data concurrently with the performing of the one or more operations on the mining material further comprises measuring spectroscopic data as the mining material is separated in a primary separation cell unit.

18. The method of claim 1, further comprising:
communicating the one of the mine face spectroscopic data, the stage spectroscopic data, and any combination thereof to a control unit; and
displaying one or more notifications with the control unit based on the one of the mine face spectroscopic data, the stage spectroscopic data, and any combination thereof.

* * * * *